(12) United States Patent
Jallad et al.

(10) Patent No.: US 8,865,128 B2
(45) Date of Patent: *Oct. 21, 2014

(54) FOLATE TARGETED ENHANCED TUMOR AND FOLATE RECEPTOR POSITIVE TISSUE OPTICAL IMAGING TECHNOLOGY

(71) Applicant: Endocyte, Inc, West Lafayette, IN (US)

(72) Inventors: Karim N. Jallad, West Lafayette, IN (US); Michael D. Kennedy, West Lafayette, IN (US); Philip S. Low, West Lafayette, IN (US); Dor Ben-Amotz, West Lafayette, IN (US)

(73) Assignee: Endocyte, Inc., West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/723,350

(22) Filed: Dec. 21, 2012

(65) Prior Publication Data

US 2013/0344002 A1 Dec. 26, 2013

Related U.S. Application Data

(63) Continuation of application No. 13/468,010, filed on May 9, 2012, now abandoned, which is a continuation of application No. 13/279,849, filed on Oct. 24, 2011, now abandoned, which is a continuation of application No. 10/360,001, filed on Feb. 6, 2003, now Pat. No. 8,043,602.

(60) Provisional application No. 60/355,417, filed on Feb. 7, 2002.

(51) Int. Cl.
*A61K 49/00* (2006.01)
*G01N 33/82* (2006.01)
*G01N 33/574* (2006.01)
*G01N 21/64* (2006.01)

(52) U.S. Cl.
CPC ............ *A61K 49/0052* (2013.01); *G01N 33/82* (2013.01); *A61K 49/0032* (2013.01); *G01N 33/57496* (2013.01); *G01N 33/57484* (2013.01); *G01N 21/6486* (2013.01); *A61K 49/0043* (2013.01)
USPC ......................................................... 424/9.1

(58) Field of Classification Search
None
See application file for complete search history.

(56) References Cited

U.S. PATENT DOCUMENTS

| 2,816,110 | A | 12/1957 | Sletzinger et al. |
| 4,577,636 | A | 3/1986 | Spears |
| 4,641,650 | A | 2/1987 | Mok |
| 4,713,249 | A | 12/1987 | Schroder |
| 4,718,417 | A | 1/1988 | Kittrell et al. |
| 4,785,806 | A | 11/1988 | Deckelbaum |
| 4,817,601 | A | 4/1989 | Roth et al. |
| 4,850,351 | A | 7/1989 | Herman et al. |
| 4,917,084 | A | 4/1990 | Sinofsky |
| 4,950,266 | A | 8/1990 | Sinofsky |
| 5,094,848 | A | 3/1992 | Brixner |
| 5,108,921 | A | 4/1992 | Low et al. |
| 5,140,104 | A | 8/1992 | Coughlin et al. |
| 5,192,525 | A | 3/1993 | Yang et al. |
| 5,217,456 | A | 6/1993 | Narciso |
| 5,266,333 | A | 11/1993 | Cady et al. |
| 5,275,594 | A | 1/1994 | Baker et al. |
| 5,336,506 | A | 8/1994 | Josephson et al. |
| 5,373,093 | A | 12/1994 | Vallarino et al. |
| 5,399,338 | A | 3/1995 | Born et al. |
| 5,416,016 | A | 5/1995 | Low et al. |
| 5,417,982 | A | 5/1995 | Modi |
| 5,547,668 | A | 8/1996 | Kranz et al. |
| 5,552,545 | A | 9/1996 | Pearce et al. |
| 5,562,100 | A | 10/1996 | Kittrell et al. |
| 5,576,305 | A | 11/1996 | Ratcliffe |
| 5,688,488 | A * | 11/1997 | Low et al. ..................... 424/1.69 |
| 5,753,631 | A | 5/1998 | Paulson et al. |
| 5,759,546 | A | 6/1998 | Weinberg et al. |
| 5,820,847 | A | 10/1998 | Low et al. |
| 6,093,382 | A | 7/2000 | Wedeking et al. |
| 6,167,297 | A | 12/2000 | Benaron |
| 6,204,371 | B1 | 3/2001 | Levinson |
| 6,217,847 | B1 | 4/2001 | Contag et al. |
| 6,221,334 | B1 | 4/2001 | Wedeking et al. |
| 6,246,901 | B1 | 6/2001 | Benaron |
| 6,270,766 | B1 | 8/2001 | Feldman et al. |
| 6,335,434 | B1 | 1/2002 | Guzaev et al. |
| 6,365,362 | B1 | 4/2002 | Terstappen et al. |
| 6,387,350 | B2 | 5/2002 | Goldenberg |
| 6,507,747 | B1 | 1/2003 | Gowda et al. |
| 6,780,984 | B2 | 8/2004 | Wang et al. |
| 6,782,289 | B1 | 8/2004 | Strauss |

(Continued)

FOREIGN PATENT DOCUMENTS

| CA | 2520406 | 10/2004 |
| CA | 2666234 | 5/2008 |

(Continued)

OTHER PUBLICATIONS

Achilefu et al., Invest. Radiology, 2000, 35(8): 479-485.*

(Continued)

*Primary Examiner* — Hong Sang
(74) *Attorney, Agent, or Firm* — Barnes & Thornburg LLP

(57) ABSTRACT

A method of differentiating tumors from healthy cells in tissue is disclosed. The method includes the steps of providing a marker-folate conjugate, placing the marker-folate conjugate in contact with the tissue and viewing the tissue.

15 Claims, 13 Drawing Sheets

(56) References Cited

U.S. PATENT DOCUMENTS

| | | |
|---|---|---|
| 6,960,449 B2 | 11/2005 | Wang et al. |
| 7,033,594 B2 | 4/2006 | Low et al. |
| 7,128,893 B2 | 10/2006 | Low et al. |
| 7,223,380 B2 | 5/2007 | Yang et al. |
| 7,381,535 B2 | 6/2008 | Perez et al. |
| 7,601,332 B2 | 10/2009 | Vlahov |
| 7,740,854 B2 | 6/2010 | Low et al. |
| 7,977,058 B2 | 7/2011 | Low et al. |
| 8,043,602 B2 | 10/2011 | Jallad et al. |
| 8,043,603 B2 | 10/2011 | Kennedy et al. |
| 8,383,354 B2 | 2/2013 | Low et al. |
| 8,388,977 B2 | 3/2013 | Low et al. |
| 8,586,595 B2 | 11/2013 | Low et al. |
| 2001/0031252 A1* | 10/2001 | Low et al. ............... 424/85.2 |
| 2002/0127181 A1 | 9/2002 | Edwards et al. |
| 2002/0192157 A1 | 12/2002 | Low et al. |
| 2003/0162234 A1 | 8/2003 | Jallad et al. |
| 2003/0198643 A1 | 10/2003 | Lu |
| 2003/0219375 A1 | 11/2003 | Piwnica-Worms |
| 2004/0033195 A1 | 2/2004 | Leamon et al. |
| 2004/0057900 A1 | 3/2004 | Edwards et al. |
| 2004/0136910 A1 | 7/2004 | Kennedy et al. |
| 2004/0184990 A1 | 9/2004 | Larsen et al. |
| 2004/0242582 A1 | 12/2004 | Green et al. |
| 2005/0002942 A1 | 1/2005 | Vlahov et al. |
| 2005/0026866 A1 | 2/2005 | Pawelek |
| 2005/0227985 A9 | 10/2005 | Green et al. |
| 2005/0244336 A1 | 11/2005 | Low |
| 2006/0002891 A1 | 1/2006 | Pouletty |
| 2006/0067946 A1 | 3/2006 | Low et al. |
| 2006/0134002 A1 | 6/2006 | Lin |
| 2006/0182687 A1 | 8/2006 | Yang et al. |
| 2006/0204565 A1 | 9/2006 | Low et al. |
| 2007/0009434 A1 | 1/2007 | Low et al. |
| 2007/0031334 A1 | 2/2007 | Leamon |
| 2007/0231266 A1 | 10/2007 | Low et al. |
| 2007/0276231 A1 | 11/2007 | Low et al. |
| 2008/0119475 A1 | 5/2008 | Low et al. |
| 2008/0138396 A1 | 6/2008 | Low et al. |
| 2008/0254499 A1 | 10/2008 | Low et al. |
| 2009/0012009 A1 | 1/2009 | Low et al. |
| 2010/0055735 A1 | 3/2010 | Low et al. |
| 2010/0322854 A1 | 12/2010 | Low et al. |
| 2011/0044897 A1 | 2/2011 | Low et al. |
| 2011/0189086 A1 | 8/2011 | Low et al. |
| 2012/0003151 A1 | 1/2012 | Low et al. |
| 2012/0276191 A1 | 11/2012 | Low et al. |
| 2013/0101519 A1 | 4/2013 | Low et al. |
| 2013/0336895 A1 | 12/2013 | Jallad et al. |
| 2013/0344002 A1 | 12/2013 | Jallad et al. |
| 2014/0056809 A1 | 2/2014 | Low et al. |
| 2014/0065066 A1 | 3/2014 | Low et al. |
| 2014/0112866 A1 | 4/2014 | Low et al. |

FOREIGN PATENT DOCUMENTS

| | | |
|---|---|---|
| EP | 0220030 | 10/1986 |
| EP | 0273085 | 12/1986 |
| EP | 1940473 | 7/2008 |
| JP | 2774378 | 7/1998 |
| JP | 2003-515570 | 5/2003 |
| JP | 2003-534388 | 11/2003 |
| RU | 2123338 | 11/1996 |
| RU | 2101703 | 10/1998 |
| WO | 90/12096 | 10/1990 |
| WO | 91/19501 | 12/1991 |
| WO | 91/19502 | 12/1991 |
| WO | 92/13572 | 2/1992 |
| WO | 96/22521 | 7/1996 |
| WO | 96/36367 | 11/1996 |
| WO | 97/37690 | 10/1997 |
| WO | 98/49196 | 11/1998 |
| WO | 99/41285 | 8/1999 |
| WO | 00/73332 | 12/2000 |
| WO | 01/19320 | 3/2001 |
| WO | 01/39806 | 6/2001 |
| WO | 01/47552 | 7/2001 |
| WO | 01/74382 | 10/2001 |
| WO | 01/91807 | 12/2001 |
| WO | 02/087424 | 11/2002 |
| WO | 2004/044227 | 5/2004 |
| WO | 2004/069159 | 8/2004 |
| WO | 2004/110250 | 12/2004 |
| WO | 2005/049579 | 6/2005 |
| WO | 2005/067644 | 7/2005 |
| WO | 2005/087275 | 9/2005 |
| WO | 2006/012527 | 2/2006 |
| WO | 2006/034046 | 3/2006 |
| WO | 2006/065943 | 6/2006 |
| WO | 2006/071754 | 7/2006 |
| WO | 2006/101845 | 9/2006 |
| WO | 2007/001466 | 1/2007 |
| WO | 2007/006041 | 1/2007 |
| WO | WO 2007/038346 | 4/2007 |
| WO | 2008/057437 | 5/2008 |
| WO | 2008/098112 | 8/2008 |
| WO | 2008/148001 | 12/2008 |
| WO | 2009/002993 | 12/2008 |
| WO | 2009/026177 | 2/2009 |

OTHER PUBLICATIONS

Leamon et al., DDT:Jan. 2001, 61(1):44-51.*
Stummer et al (J Neurosurg., 2000, 93:1003-1013.*
U.S. Appl. No. 61/235,220, filed Aug. 19, 2009, Low et al.
U.S. Appl. No. 61/157,847, filed Mar. 5, 2009, Low et al.
NCBI, MeSH definition for Indocarbocyanine Green, 2 pages, Aug. 31, 2008.
"Macrophages" from Wikipedia, updated Nov. 18, 2007.
Achilefu et al., "Novel Receptor-Targeted Fluorescent Contrast Agents for in Vivo Tumor Imaging", Investigative Radiology, vol. 35, No. 8, pp. 479-485, Aug. 2000.
Antohe et al., "Increased uptake of folate conjugates by activated macrophages in experimental hyperlipemia", Cell Tissue Research, vol. 320, No. 2, pp. 277-285, May 2005.
Aviram et al., "Intralipid infusion abolishes ability of human serum to cholesterol-load cultured macrophages", Arteriosclerosis, vol. 9, pp. 67-75, 1989.
Ballou et al., "Tumor labeling in vivo using cyanine-conjugated monoclonal antibodies", Cancer Immunol Immunother, vol. 41, pp. 257-263, 1995.
Barrera et al., "Synovial macrophage depletion with clodronate-containing liposomes in rheumatoid arthritis", Arthritis and Rheumatism, vol. 43, pp. 1951-1959, 2000.
Beaumont et al., "Selective Fluorodenitration of Chloronitroaromatics", J. Fluorine Chem., vol. 63, pp. 25-30, 1993.
Becker et al., "Macromolecular Contrast Agents for Optical Imaging of Tumors: Comparison of Indotricarbocyanine-labeled Human Serum Albumin and Transferrin", Photochemistry and Photobiology, vol. 72, No. 2, pp. 234-241, May 14, 2000.
Bettio et al, "Synthesis and Preclinical Evaluation of a Folic Acid Derivative Labeled with 18F for PET Imaging of Folate Receptor-Positive Tumors", The Journal of Nuclear Medicine, vol. 47, No. 7, pp. 1153-1160, 2006.
Bock et al., "Sulfonamide Structure-Activity Relationships in a Cell-Free System. 2. Proof for the Formation of a Sulfonamide-Containing Folate Analog", Journal of Medicinal Chemistry, vol. 17, No. 1, pp. 23-28, 1974.
Boechat et al., Fluorodenitrations Using Tetramethylammonium Fluoride, J. Soc. Chem, Commun., pp. 921-992, 1993.
Boente et al., "Screening, imaging, and Early Diagnosis of Ovarian Cancer", Clinical Obstetrics and Gynecology, vol. 37, No. 2, pp. 377-391, Jun. 1994.
Bonasera et al., "The Synthesis of [26, 27-11C]Dihydroxyvitamin D3, a Tracer for Positron Emission Tomography (PET), Bioorganic & Medicinal Chemistry", Elsevier Science Ltd., vol. 9, pp. 3123-3128, 2001.

(56) References Cited

OTHER PUBLICATIONS

Budinger et al., "New Approaches to Targeting Arthritis with Radiopharmaceuticals", The Journal of Rheumatology, 22(1) Supp: 62-67, 1995.
Burke et al., "Book Review. The Macrophage", British Journal of Cancer, vol. 89, p. 421, 2003.
Campbell et al., "Folate-binding Protein is a Marker for Ovarian Cancer", Cancer Research, vol. 51, pp. 5329-5338, Oct. 1991.
Canis et al., "Lapascopic Diagnosis of Adnexal Cystic Masses: A 12-Year Experience With Long-Term Follow-Up", Obstetrics & Gynecology, vol. 83, No. 5, pp. 707-712, May 1994.
U.S. Appl. No. 12/526,096, filed Aug. 6, 2009, Low et al.
Case, "Ultrasound Physics and Instrumentation, Surgical Clinics of North America", vol. 78, No. 2, pp. 197-217, Apr. 1998.
Chen et al., "MicroPET Imaging of Brain Tumor Angiogenesis with 18F-Labeled PEGylated RGD Peptide", European Journal of Nuclear Medicine and Molecular Imaging, vol. 31, No. 8, pp. 1081-1089, Aug. 2004.
Tung et al., "Preparation of a Cathepsin D Sensitive Near-Infrared Fluorescence Probe for Imaging", American Chemical Society, vol. 10, No. 5, pp. 692-696, 1999.
Cochlovius, "Therapeutic Antibodies", Modern Drug Discovery, pp. 33-38, 2003.
Cohen et al., "Screening for ovarian cancer: The role of noninvasive imaging techniques", Am J. Obstet Gynecol., vol. 170, No. 4, pp. 1088-1094, 1994.
Cohen et al., "Three-Dimensional Power Doppler Ultrasound Improves the Diagnostic Accuracy for Ovarian Cancer Prediction", Gynecologic Oncology, vol. 82, pp. 40-48, 2001.
Cox et al., "Anhydrous, Tetrabutylammonium Fluoride: A Mild but Highly Efficient Source of Nucleophilic Fluoride Ion", J. Org. Chem., No. 49, pp. 3216-3219, 1984.
Degrado et al., "Synthesis and Evaluation of (18)F-Labeled Choline Analogs as Oncologic PET Tracers", J. Nuclear Medicine, vol. 42, No. 12, pp. 1805-1814, 2001.
DePriest et al., "Transvaginal Sonography as a Screening Method for the Detection of Early Ovarian Cancer", Gynecologic Oncology, vol. 65, No. GO974705, pp. 408-414, 1997.
Feldman et al., "Anti-TNFa Therapy Is Useful in Rheumatoid Arthritis and Crohn's Disease: Analysis of the Mechanism of Action Predicts Utility in Other Diseases", Transplant. Proc. , 30, pp. 4126-4127, 1998.
Forstner et al., "CT and MRI of ovarian cancer", Abdominal Imaging, vol. 20, pp. 2-8, 1995.
Garg et al., "Fluorine-18 Labeling of Monoclonal Antibodies and Fragments with Preservation of Immunoreactivity", Bioconjugate Chem., vol. 2, No. 1, pp. 44-49, 1991.
Giroldo et al., "An Unusually Fast Nucleophilic Aromatic Displacement Reaction: The Gas-Phase Reaction of Fluoride Ions with Nitrobenzene", Angew. Chem. Int. Ed., No. 43, pp. 3588-3590, 2004.
Godwin et al., "The synthesis of biologically active pteroyloligo-g-L-glutamates (folic acid conjugates): Evaluation of (3H) pteroylheptaglutamate for metabolic studies", Journal of Biological Chemistry. vol. 247, pp. 2266-2271, Apr. 1974.
Gotoh, "Causes and treatment of rheumatoid arthritis; recent trend I. Progress in pathogenesis of rheumatoid arthritis; role of macrophages and dendritic cells", Pharma Nedica, Japan Medical Review Co., Ltd., Tokyo, 17(10): 35-39, 1999.
Greenman, Y., et al., "Heterogeneous Expression of Two Somatostatin Receptor Subtypes in Pituitary Tumors," Journal of Clinical Endocrinology and Metabolism, vol. 78, No. 2, pp. 398-403, 1994.
Hamacher et al., "No-Carrier-Added Nucleophilic 18F-Lavelling in an Electrochemical Cell Exemplified by the Routine Production of [18F]altanserin", Applied Radiation and Isotopes, No. 64, pp. 989-994, 2006.
Harris et al., "Human leukemic models of myelomonocytic development: a review of the HL-60 and U937 cell lines", Journal of Leukocyte Biology, vol. 37., No. 4, pp. 407-422, 1985.

Holmgren et al., "Strategies for the Induction of Immune Responses At Mucosal Surfaces Making Use of Cholera Toxin B Subunit As Immunogen, Carrier, and Adjuvant", Am. J. Trop Med Hyd, 50, pp. 42-54, 1994.
Hynes et al., "Quinazolines as Inhibitors of Dihydrofolate Reductase. 4. Classical Analogues of Folic and Isofolic Acids", Journal of Medicinal Chemistry, vol. 20, No. 4, pp. 588-591, 1977.
Jager et al., "Resection guided by antibodies (REGAJ): a diagnostic procedure during second-look operation in ovarian cancer patients", Depts of Obstetrics, Gynecology and Nuclear Medicine, Univ of Erlangen-Nurnberg, pp. 18-20, 1990.
Johnstrom et al., "18F-Endothelin-1, a Positron Emission Tomography (PET) Radioligand for the Endothelin Receptor System: Radiosynthesis and In Vivo Imaging Using MicroPET", Clinical Science, vol. 103, Suppl. 48, pp. 45-85, 2002.
Karlan, "The Status of Ultrasound and Color Doppler Imaging for the Early Detection of Ovarian Cancer", Cancer Investigation, vol. 15, No. 3, pp. 265-269, 1997.
Karlan et al., "Ovarian Cancer Screening: The Role of Ultrasound in Early Detection", Cancer Supplement, vol. 76, No. 10, pp. 2011-2015, Nov. 1995.
Karsten et al., "Towards Usage-Based Accounting: Applying Policy-Based Intelligent Agents, ITC 15". Elsevier Science B.V., pp. 633-642, 1997.
Kennedy et al., "Evaluation of Folate Conjugate Uptake and Transport by the Choroid Plexus of Mice", Pharmaceutical Research, vol. 20, No. 5, p. 714-719, May 2003.
Kennedy et al., "Optical imaging of metastatic tumors using a folate-targeted fluorescent probe", J. of Biomedical Optics, vol. 8, No. 4, pp. 636-641, Oct. 2003.
Kim et al., "Synthesis and Biological Activity of 10-Thia-10-deaza Analogs of Folic Acid, Pteroic Acid, and Related Compounds", Journal of Medicinal Chemistry, vol. 18, No. 8, pp. 776-780, 1975.
Kinne et al., "Macrophage in rheumatoid arthritis", Arthritis Research , vol. 2, No. 3, pp. 189-202, 2000.
Konda et al., "Development of a Tumor-Targeting MR Contrast Agent Using the High-Affinity Folate Receptor", Investigative Radiology, vol. 35, No. 1, pp. 50-57, 2000.
Kramer, "Basic Principles of Magnetic Resonance Imaging", Radiological Clinics of North America, vol. 22, No. 4, pp. 765-778, Dec. 1984.
Kuroiwa et al., "Development of a Fluorescein Operative Microscope for Use During Malignant Glioma Surgery", Elsevier Science Inc., vol. 50, pp. 41-49, 1998.
Leamon et al., "Folate-mediated targeting: from diagnosis to drug and gene therapy", DDT vol. 6 No. 1 44-51, Jan. 2001.
Leamon et al., "Synthesis and Biological Evaluation of EC140: A Novel Folate—Targeted Cinca Alkaloid Conjugate", Bioconjugate Chem., vol. 17, No. 5, pp. 1226-1232, 2006.
Leamon et al., "Synthesis and Biologicial Evaluation of EC20: A New Folate-Derived, 99mTc-Based Radiopharmaceutical", Bioconjugate Chemistry, vol. 13, No. 6, pp. 1200-1210, 2002.
Leamon et al., "Selective Targeting of Malignant Cells with Cytotoxin-Folate Conjugates", J. Drug Targeting 2: 101-112, 1994.
U.S. Appl. No. 60/956,489, filed Aug. 17, 2007, Low et al.
Lee et al., "Folic Acid Antagonists. Methotrexate Analogs Containing Spurious Amino Acids. Dichlorohomofolic Acid", Journal of Medicinal Chemistry, vol. 17, No. 3, pp. 326-330, 1974.
Lemaire et al., "Fluorine-18-Altanserin: A Radioligand for the Study of Serotonin Receptors with PET: Radiolabeling and in Vivo Biologic Behavior in Rats", The Journal of Nuclear Medicine. vol. 32, No. 12, pp. 2266-2272, Dec. 1991.
Licha et al., "Hydrophilic Cyanine Dyes as Contrast Agents for Near-infrared Tumor Imaging: Synthesis, Photophysical Properties and Spectroscopic in vivo Characterization", Photochemistry and Photobiology, vol. 72, No. 3, pp. 392-398, 2000.
Liotta et al., "The Chemistry of "Naked" Anions. I. Reactions of the 18-Crown-6 Complex of Potassium Fluoride with Organic Substrates in Aprotic Organic Solvents", Journal of American Chemical Society, vol. 96, No. 7, pp. 2250-2252, Apr. 3, 1974.

(56) References Cited

OTHER PUBLICATIONS

Liu-Wu et al., "Identification and Analysis of Macrophage-Derived Foam Cells from Human Atherosclerotic Lesions by Using a 'Mock' FL3 Channel in Flow Cytometry", Cytometry, vol. 29, No. 2, pp. 155-164, 1997.

Low et al., "Ovarian Cancer: Comparison of findings with Perfluorocarbon-enhanced MR Imaging, In-111-CYT-103 Immunoscintigraphy, and CT", Depts of Diagnostic Rad and Onc, Sharp Memorial Hospital, vol. 195, No. 2, pp. 391-400, 1995.

Lu et al., "Folate-Targeted Enzyme Prodrug Cancer Therapy Utilizing Penicillin-V Amidase and a Doxorubicin Prodrug", J. Drug Targeting 7:43-53, 1999.

Mahmood et al, "Near Infrared Optical Imaging for Protease Activity for Tumor Detection", Radiology, 213:866-870, 1999.

Maiman et al., "Laproscopic Excision of Ovarian Neoplasm Subsequently Found to Be Malignant", Obstetrics & Gynecology, vol. 77, No. 4, pp. 563-565, Apr. 1991.

Mancini et al., "Relative contributions of apolipoprotein A and apolipoprotein B to the development of fatty lesions in the proximal aorta of mice", Arterioscler. Thromb. Vasc. Biol., vol. 15, pp. 1911-1916, 1995.

Mantovani et al., "Folate Binding Protein Distribution in Normal Tissues and Biological Fluids From Ovarian Carcinoma Patients as Detected by the Monoclonal Antibodies Mov 18 and Mov 19", European Journal of Cancer, 1994, 30A(3):363-9.

Mathias et al., "Preparation of 66Ga- and 68GA-labeled Ga(III)-deferoxamine-folate as potential folate-receptor-targeted PET radiopharmaceuticals", Nuclear Medicine and Biology, vol. 30, pp. 725-731, 2003.

Matsuyama et al., "Clinical significance of the folate receptor beta expression in rheumatoid synovial macrophages", Rheumatoid, Japan College of Rheumatology, 41(2): 265, 2001.

Matsuyama et al., "Activation and pathological significance of macrophages in rheumatoid synovitis", Clinical Immunity, Japan, Kagaku Hyoronsha, Tokyo, 30(2): 214-219, 1998.

Mestas et al. "Of Mice and Not Men: Differences between Mouse and Human Immunology", J. of Immunology, 172, pp. 2731-2738, 2004.

Mukasa et al., "Function analysis of folate receptor-β in a RA synovial membrane macrophage cell line", Rheumatoid, Japan College of Rheumatology, 40(2): 378, 2000.

Mulherin et al., "Synovial tissue macrophage populations and articular damage in rheumatoid arthritis", Arthritis and Rheumatism, vol. 39, No. 1, pp. 115-124, 1996.

Murakami et al., "18F-Labelled Annexin V: A PET Tracer for Apoptosis Imaging", European Journl of Nuclear Medicine and Molecular Imaging, vol. 31, No. 4, pp. 469-474, Apr. 2004.

Nagayoshi et al., "Effectiveness of Anti-Folate Receptor β Antibody Conjugated with Truncated *Pseudomonas* Exotoxin in the Targeting of Rheumatoid Arthritis Synovial Macrophages", Arthritis and Rheumatism, vol. 52, pp. 2666-2675, Sep. 2005.

Nair et al., "Folate Analogues Altered in the C9-N10 Bridge Region. 10-Oxafolic Acid and 10-Oxaaminopterin", Journal of Medicinal Chemistry, vol. 19, No. 6, pp. 825-829, 1976.

Nair et al., "Folate Analogues Altered in the C9-N10 Bridge Region: N10-Tosylisohomofolic Acid and N10-Tosylisohomoaminopterin", Journal of Medicinal Chemistry, vol. 21, No. 7, pp. 673-677, 1978.

Nair et al., "Folate Analogues Altered in the C9-N10 Bridge Region: 11-Thiohomofolic Acid", Journal of Medicinal Chemistry, vol. 22, No. 7, pp. 850-855, 1979.

Nair et al., "Folate Analogues Altered in the C9-N10 Bridge Region. 14. 11-Oxahomofolic Acid, a Potential Antitumor Agent", Journal of Medicinal Chemistry, vol. 23, pp. 59-65, 1980.

Nair et al., "Folate Analogues Altered in the C9-N10 Bridge Region. 18. Synthesis and Antitumor Evaluation of 11-Oxahomoaminopterin and Related Compounds", Journal of Medicinal Chemistry, vol. 24, pp. 1068-1073, 1981.

Nair et al., "Folate Analogues. 20. Synthesis and Antifolate Activity of 1, 2, 3, 4, 5, 6,—Hexahydrohomofolic Acid", Journal of Medicinal Chemistry, vol. 26, pp. 135-140, 1983.

Nair et al., "Folate Analogues. 21. Synthesis and Antifolate and Antitumor Activities of N10-(Cyanomethyl)-5,8-dideazafolic Acid", Journal of Medicianal Chemistry, vol. 26, pp. 605-607, 1983.

Nair et al., "Folate Analogues. 22. Synthesis and Biological Evaluation of Two Analogues of Dihydrofolic Acid Processing a 7,8-Dihydro-8-oxapterin Ring System", Journal of Medicinal Chemistry, vol. 26, 1164-1168, 1983.

U.S. Appl. No. 14/187,844.

Nakashima-Matsushita et al, "Selective expression of folate receptor beta and its possible role in methotrexate transport in synovial macrophages from patients with rheumatoid arthritis", Arthritis Rheum. 42(8): 1609-1616, 1999.

Nehzat et al. "Four ovarian cancers diagnosed during laproscopic management of 1011 women with adnexal masses", Am J Obstet Gynecol., vol. 167, No. 3, pp. 790-796, Sep. 1992.

Oatis et al., "Synthesis of Quinazoline Analogues of Folic Acid Modified at Position 10", Journal of Medicinal Chemistry, vol. 20, No. 11, pp. 1393-1396, 1977.

Olma et al., "4-[18F]fluorophenyl ureas via carbamate-4-nitrophenyl esters and 4-[18F]Fluoroaniline", Journal of Labeled Compd. And Radiopnarm, vol. 49, pp. 1037-1050, 2006.

Paigen et al., "Variation in susceptibility to atherosclerosis among inbred strains of mice", Atherosclerosis, vol. 57, No. 1, pp. 65-73, 1985.

Pasterkamp et al. "Techniques characterizing the coronary atherosclerotic plaque: Influence on clinical decision making?", J. Amer. Coll. Cardiol. 36:13-21, 2000.

Paulos et al. "Folate Receptor-Mediated Targeting of Therapeutic and Imaging Agents to Activated Macrophages in Rheumatoid Arthritis", Advanced Drug Delivery Reviews, vol. 56, No. 8, pp. 1205-1217, 2004.

Pelegrin et al., "Antibody-Fluorescein Conjugates for Photoimmunodiagnosis of Human Colon Carcinoma in Nude Mice", Institute of Biochemistry, University of Lausanne, vol. 67, No. 10, pp. 2529-2537, 1991.

Plante et al., "Polyglutamyl and Polylysyl Derivatives of the Lysine Analogues of Folic Acid and Homofolic Acid", Journal of Medicinal Chemistry, vol. 19, No. 11, pp. 1295-1299, 1976.

Rampone et al., "Ovarian cancer screening by transvaginal color Doppler ultrasonography", Minerva Ginecologica, vol. 53, Suppl. 1 al N 1, pp. 125-128, 2001.

Reddy et al., "Optimization of Folate-Conjugated Liposomal Vectors for Folate Receptor-Mediated Gene Therapy", J. Pharm. Sciences 88: 1112-1118, 1999.

Reddy et al., "Folate-Mediated Targeting of Therapeutic and Imaging Agents to Cancers", Critical Reviews in Ther. Drug Carrier Systems 15: 587-627, 1998.

Reddy et al., " Folate receptor specific anti-tumor activity of folate-mitomycin conjugates", Cancer Chemother. Pharmacol., 58(2): 229-36, 2006.

Reles et al., "Transvaginal Color Doppler Sonography and Conventional Sonography in the Preoperative Assessment of Adnexal Masses", Journal of Clinical Ultrasound, vol. 25, No. 5, pp. 217-225, Jun. 1997.

Roberts, et al., "Folic Acid Analogs. Modifications in the Benzene-Ring Region. 3. Neohomofolic and Neobishomofolic Acids. An Improved Synthesis of Folic Acid and Its Analogs". Journal of Medicinal Chemistry, 1973, 16(6): 697-9.

Roberts et al., "Folic Acid Analogs. Modifications in the Benzene-Ring Region. 2. Thiazole Analogs", Journal of Medicinal Chemistry, 15 (12): 1310-1312, 1972.

Roberts et al., "Folic Acid Analogs. Modifications in the Benzene-Ring Region. 1. 2'- and 3'-Azafolic Acids", Journal of Medicinal Chemistry, 14(2): 125-130, 1971.

Roberts et al., "Folic Acid Analogs. Modifications in the Benzene-Ring Region. 4. 3'- Ethyl - and 3'- Isopropylfolic Acids", Journal of Medicinal Chemistry, vol. 17, No. 2, pp. 219-222, 1974.

Rouzi et al., "Lapascopic Ovarian Cystectomy: Selection of Patients and Consequences of Rupture of Ovarian Malignancy", Annals of Saudi Medicine, vol. 17, No. 3, pp. 321-325, 1997.

Rudd et al., "Imaging Atherosclerotic Plaque Inflammation with [<18>F]-Fluorodeoxyglucose Positron Emission Tomography", Circulation, vol. 105, No. 23, pp. 2709-2710, 2002.

(56) References Cited

OTHER PUBLICATIONS

Sato et al., "Usefulness of Mass Screening for Ovarian Carcinoma Using Transvaginal Ultasonography", American Cancer Society, vol. 89, No. 3, pp. 582-588, Aug. 2000.
Sevick-Muraca et al., "Fluorescence and Absorption Contrast Mechanisms for Biomedical Optical Imaging Using Frequency-Domain Techniques", Photochemistry and Photobiology, vol. 66, No. 1, pp. 55-64, 1997.
Sheski et al., "Endoscopic Treatment of Early-Stage Lung Cancer", Division of Pulmonary, Allergy, Care, and Occupational Medicine at IU School of Medicine, vol. 7, No. 1, pp. 35-44, Jan./Feb. 2000.
Shoup et al., "Synthesis of Fluorine-18-Labeled Biotin Derivatives: Biodistribution and Infection Localization", J. Nuclear Medicine, vol. 35, No. 10, pp. 1685-1690, 1994.
Sijtsema et al., "Confocal Direct Imaging Raman Microscope: Design and Application in Biology", Applied Spectroscopy, vol. 52, Issue 3, pp. 348-355, 1998.
Sima et al., "Experimental obstructive coronary atherosclerosis in the hyperlipidemic hamster", J Submicrosc Cytol Pathol, vol. 22, No. 1, pp. 1-16, 1990.
Simionescu et al., "Prelesional modifications of the vessel wall in hyperlipidemic atherogenesis: Extracellular accumulation of modified and reassembled lipoproteins", Ann. NY Acad. Sci., vol. 598, pp. 1-16, 1990.
Smart et al., "Protein kinase C activators inhibit receptor-mediated potocytosis by preventing internalization of caveolae", Journal of Cell Biology, vol. 124, No. 3, pp. 307-313, 1994.
Solomin et al., "Computerized Tomography in Ovarian Cancer", Gynecologic Oncology, vol. 15 pp. 48-55, 1983.
Sudimack et al., "Targeted drug delivery via the folate receptor", Advanced Drug Delivery Reviews,vol. 41, pp. 147-162, 2000.
Sun et al., "Anhydrous Tetrabutylammonium Fluoride", J. Am. Chem. Soc., vol. 127, No. 7, pp. 2050-2051, 2005.
Sun et al., "Room-Temperature Nucleophilic Aromatic Fluorination: Experimental and Theoretical Studies", Angew. Chem. Int. Ed., No. 45, pp. 2720-2725, 2006.
Sundstrum et al., "Establishment and characterization of a human histiocytic lymphoma cell line (U-937)", International Journal of Cancer, vol. 17, No. 5, pp. 565-577, 1976.
Sutcliffe-Goulden, "Solid Phase Synthesis of [18F]Labelled Peptides for Positron Emission Tomography", Bio. & Medicin. Chem. Letters, No. 10, pp. 1501-1503, 2000.
Tan et al., "A Complete Remote-Control System for Reliable Preparation of [18F]altanserin", Applied Radiation and Isotopes, vol. 50, pp. 923-927, 1999.
Temple, Jr. et al., "Synthesis of Pseudo Cofactor Analogues as Potential Inhibitors of the Folate Enzymes", Journal of Medicinal Chemistry, vol. 25, pp. 161-166, 1982.
Toffoli et al., "Expression of Folate Binding Protein as a Prognostic Factor for Response to Platinum-Containing Chemotherapy and Survival in Human Ovarian Cancer", Int. J. Cancer, vol. 79, pp. 121-126, 1998.
Toffoli et al., "Overexpression of Folate Binding Protein in Ovarian Cancers", Int. J. Cancer (Pred. Oncol.), vol. 74., pp. 193-198, 1997.
Turk et al., "Folate-targeted imaging of activated macrophage in rats with adjuvant-induced arthritis", Arthritis and Rheumatism, vol. 46, No. 7, pp. 1947-1955, 2002.
Urban, "Screening for ovarian cancer: We now need a definitive randomized trial", BMJ, vol. 319, pp. 1317-1318, Nov. 1999.
Van Noort et al., "Cell Biology of Autoimmune Diseases", International Review of Cytology, vol. 178, pp. 127-204, 1998.
Vo-Dinh et al., "In Vivo Cancer Diagnosis of the Esophagus Using Differential Normalized Fluorescence (DNF) Indices", Lasers in Surgery and Medicine, vol. 16, pp. 41-47, 1995.
Wang et al., "Chemokines and their role in cardiovascular diseases", TCM, vol. 8, pp. 169-174, 1998.
Wang et al. "Synthesis, Purification, and Tumor Cell Uptake of Ga-Deferoxamine-Folate, a Potential Radiopharmaceutical for Tumor Imaging", American Chemical Society, Bioconjugate Chem., 1996, 7(1): 56-62, 1996.
Weinstock et al., "Folic Acid Analogs. II. p-{[2,6-Diamino-8-purinyl)methyl]amino}—benzoyl-L-glutamic Acid and Related Compounds", Journal of Medicinal Chemistry, 1970, 13(5): 995-997, 1970.
Weissleder et al., "In vivo imaging of tumors with protease-activated near-infrared fluorescent probes", Nature Biotechnology, vol. 17, pp. 375-378, Apr. 1999.
Weitman et al., "The folate receptor in central nervous system malignancies of childhood", Journal of Neuro-Oncology, vol. 21, pp. 107-112, 1994.
Westerhof et al., Carrier-and Receptor-Mediated Transport of Folate Antagonists Targeting Folate-Dependent Enzymes: Correlates of Molecular-Structure and Biological Activity, Molecular Pharmacology, 1995, 48: 459-471, 1995.
Whitehurst et al., "Development of an alternative light source to lasers for biomedical applications", SPIE, vol. 2629, pp. 291-298, 1993.
Wu et al., "Expression of Folate Receptor Type a in Relation to Cell Type Malignancy, and Differentiation in Ovary, Uterus and Cervix", Cancer Epidemiology, Biomarkers & Prevention, vol. 8, pp. 775-782, 1999.
Yavorsky et al., "Antiparticles", Handbook on Physics, pp. 339-340, 1984.
Zeisel et al., "Choline, an Essential Nutrient for Humans", The Faseb Journal, vol. 5, No. 7, pp. 2093-2098, 1991.
Delaloye et al., "Tumor imaging with monoclonal antibodies", Seminars in Nuclear Medicine, 25:144-164, 1995.
Reubi, "The role of peptides and their receptors as tumor markers", Endocrinology & Metabolism Clinics of North America, 22: 917-939, 1993.
Garin-Chesa et al., "Trophoblast and ovarian cancer antigen LK26. Sensitivity and specificity in immunopathology and molecular identification as a folate-binding protein", American Journal of Pathology, 142: 557-567, 1993.
Patrick et al., "Folate receptors as potential therapeutic targets in choroid plexus tumors of SV40 transgenic mice", Journal of Neuro-Oncology, 32: 111-123, 1997.
Weitman et al., "Distribution of the folate receptor GP38 in normal and malignant cell lines and tissues", Cancer Research, 52: 3396-3401, 1992.
Mathias et al., "Indium-111-DTPA-folate as a potential folate-receptor-targeted radiopharmaceutical", Journal of Nuclear Medicine, 39: 1579-1585, 1998.
Acosta et al., "Chromoendoscopy—where is it useful?", Journal of Clinical Gastroenterology, 27:13-20,1998.
Fleischer, "Chromoendoscopy and magnification endoscopy in the colon", Gastrointestinal Endoscopy, 49: S45-49, 1999.
Stepp et al., "Fluorescence endoscopy of gastrointestinal diseases: basic principles, techniques, and clinical experience", Endoscopy, 30: 379-386, 1998.
Ballou et al., "Tumor detection and visualization using cyanine fluorochrome-labeled antibodies", Biotechnology Progress, 13: 649-658, 1997.
Licha et al., "Synthesis, characterization, and biological properties of cyanine-labeled somatostatin analogues as receptor-targeted fluorescent probes", Bioconjugate Chemistry, 12: 44-50, 2001.
Becker et al., "Receptor-targeted optical imaging of tumors with near-infrared fluorescent ligands", Nature Biotechnology, 19: 327-331, 2001.
Terpetschnig et al., "Synthesis of squaraine-N-hydroxysuccinimide esters and their biological application as long-wavelength fluorescent labels", Analytical Biochemistry, 217: 197-204, 1994.
Mujumdar et al., "Cyanine dye labeling reagents containing isothiocyanate groups", Cytometry, 10: 11-19, 1989.
Wang et al., "Design and synthesis of [111In]DTPA-folate for use as a tumor-targeted radiopharmaceutical", Bioconjugate Chemistry, 8: 673-679, 1997.
Dimartino et al., "Antiarthritic and immunoregulatory activity of spirogermanium", Journal of Pharmacology an Experimental Therapeutics, 236: 103-110, 1986.
Ross et al., "Differential regulation of folate receptor isoforms in normal and malignant tissues in vivo and in established cell lines. Physiologic and clinical implications", Cancer, 73: 2432-2443, 1994.

(56) References Cited

OTHER PUBLICATIONS

Ross et al., "Folate receptor type beta is a neutrophilic lineage marker and is differentially expressed in myeloid leukemia", Cancer, 85: 348-357, 1999.
Curtin et al., "Stage IV ovarian cancer: impact of surgical debulking", Gynecologic Oncology, 64: 9-12, 1997.
Munkarah et al., "Prognostic significance of residual disease in patients with stage IV epithelial ovarian cancer", Gynecologic Oncology, 64: 13-17, 1997.
Murolo et al., "Ultrasound examination in ovarian cancer patients. A comparison with second look laparotomy", Journal of Ultrasound in Medicine, 8: 441-443, 1989.
Piver et al., "Second-look laparoscopy prior to proposed second-look parotomy", Obstetrics and Gynecology, 55: 571, 1980.
Bell et al., "Intraoperative radioimmunodetection of ovarian cancer using monoclonal antibody B72.3 and a portable gamma-detecting probe", Obstetrics and Gynecology, 76: 607-677, 1990.
Reuter et al., "Detection of colorectal carcinomas by intraoperative RIS in addition to preoperative RIS: surgical and immunohistochemical findings", European Journal of Nuclear Medicine, 19: 102-109, 1992.
Hornung et al., "Minimally-invasive debulking of ovarian cancer in the rat pelvis by means of photodynamic therapy using the pegylated photosensitizer PEG-m-THPC", British Journal of Cancer, 81: 631-637, 1999.
Folli et al., "Immunophotodiagnosis of colon carcinomas in patients injected with fluoresceinated chimeric antibodies against carcinoembryonic antigen", Proceedings of the National Academy of Sciences of the United States of America, 89: 7973-7977, 1992.
Folli et al., "Antibody-indocyanin conjugates for immunophotodetection of human squamous cell carcinoma in nude mice", Cancer Research, 54: 2643-2649, 1994.
Bannwarth et al., "Methotrexate in rheumatoid arthritis. An update", Drugs, 47: 25-50, 1994.
Bettegowda, et al., Proc. Natl. Acad. ScL U.S.A., 102: 1145-1150, 2005.
Bunce, et al., Infect. Immun., 60: 2636-2640, 1992.
Claassen E. et al., "Preparation and characteristics of dichloromethylene diphosphonate-containing liposomes," J. Microencapsul., 3: 109-14, 1986.
Marceau et al., Bioorganics and Medical Chemistry Letters, 15(24): 5442-5445, 2005.
Novabiochem® Letters, "Resins for the synthesis of biotinylated and fluorescently-labeled peptides," Jan. 2004, pp. 1-4, 2004.
Novabiochem® Letters, "Products for peptide ligation," Feb. 2004, pp. 1-4, 2004.
Novabiochem® Letters, "Amino acids for Fmoc SPPS," Mar. 2004, pp. 1-4, 2004.
Novabiochem® Letters, "PEG reagents," Apr. 2004, pp. 1-4, 2004.
Leamon et al., "Folate-Liposome-Mediated Antisense Oligodeoxynucleotide Targeting to Cancer Cells: Evaluation in Vitro and in Vivo", Bioconjugate Chem., 14, 738-747, 2003.
Leamon et al., "Folate-mediated Drug Delivery: Effect of Alternative conjugate Chemistry", Journal of Drug Targeting, col. 7, No. 3, 157-169, 1999.
Marecos et al., "Antibody-Mediated versus Nontargeted Delivery in a Human Small Cell Lung Carcinoma Model", Bioconjugate Chemistry, 9:184-191 (1998).
"Osteomyelitis", XP-002569963, URL:http://emedicine.medscape.com/article/785020-overview>, retrieved Feb. 22, 2010.
Kennedy MD, "Folate-targeted imaging agents," Thesis submitted to the faculty of Purdue University in partial fulfillment of the requirements for the degree of Doctor of Philosophy, published Nov. 2004.
Holladay et al., "Riboflavin-mediated delivery of a macromolecule into cultured human cells," Biochim Biophys Acta 1426(1): 195-204 (1999).
Low PS, Leamon CP, Reddy JA, Green MA, Mathias C, Turk MJ, Waters DJ, Lu J, Lee RJ, Kennedy MD, "Folate-mediated delivery of therapeutic and imaging agents to cancer tissue," Gene, Drug Therapy, and Molecular Biology (Abstract), 2000.
Low, P.S., Leamon, C.P., Reddy, J.A., Green, M.A., Mathias, C., Turk, M.J., Waters, D.J., Lu, J., Lee, R.J. and Kennedy, M., "Folate-Mediated Delivery of Therapeutic and Imaging Agents to Cancer Tissues in Vivo," International Symposium on Tumor Targeted Delivery Systems, Bethesda, Maryland. British Journal of Pharmacology, vol. 134 (Abstract), 2001.
Kern, et al., "Evaluation of the Culprit Plaque and the Physiological Significance of Coronary Atherosclerotic Narrowings," Circulation, 2001; 103:3142-3149.
Phelps et al., Journal of Nuclear Medicine, 1975, 16(3): 210-224.
Snook et al., Br. J. Cancer, 1990, 62 (Suppl. X): 89-91.
Patton, Radiographics, 1998, 18: 995-1007.
Kanagaki et al., "Pituitary Gland and Parasellar Region," in Magnetic Resonance Tomography, Reiser et al. (eds.), 2008, p. 422.
Barnes, H. H., et al., "Purification of Catechol Siderophores by Boronate Affinity Chromatography: Identification of Chrysobactin From Erwinia carotovora subsp. carotovora", 1999, BioMetals, vol. 12, pp. 83-87.
Collins, Peter, et al., "Monosaccharides, Their Chemistry and Their Roles in Natural Products", 1995 Wiley Publishers, Book Reference, We will provide a copy of the book if requested.
Georgakoudi, Irene, et al., "In Vivo Flow Cytometry: A New Method for Enumerating Circulating Cancer Cells", Aug. 1, 2004, Cancer Research, No. 64, pp. 5044-5047.
Hanessian, Stephen, "Preparative Carbohydrate Chemistry", 1997 Marcel Dekker, Inc., Book Reference, We will provide a copy of the book if requested.
Idanpaan-Heikkila, Ilona, et al., "Oligosaccharides Interfere With the Establishment and Progression of Experimental Pneumococcal Pneumonia", 1997, The Journal of Infectious Diseases, No. 176, pp. 704-712.
Iijima, Masatomi, et al., "IC202A, A New Siderophore With Immunosuppressive Activity Produced by Streptoalloteichus sp. 1454-19. I. Taxonomy, fermentation, isolation and biological activity.", Jan. 1999.
Lingwood, Clifford A., "Oligosaccharide Receptors for Bacteria: A View to A Kill", 1998, Curr Opin Chem Biol., pp. 695-700.
Michelson, Alan D., et al., "Evaluation of Platelet Function by Flow Cytometry", 2000, Methods, vol. 21, pp. 259-270.
Novak, J., et al., "In Vivo Flow Cytometer for Real-Time Detection and Quantification of Circulating Cells", Jan. 1, 2004 Optics Letters, vol. 29, No. 1, pp. 77-79.
Ratledge, Colin, et al., "The Occurrence of Carboxymycobactin, The Siderophore of Pathogenic Mycobacteria, As A Second Extracellular Siderophore in Mycobacterium smegmatis", 1996 Microbiology, vol. 142, pp. 2207-2212.
Scharfman, Andree, et al., "Pseudomonas Aeruginosa Binds to Neoglycoconjugates Bearing Mucin Carbohydrate Determinants and Predominantly to sialyl-Lewis x Conjugates", 1999, Glycobiology, vol. 9, No. 8, pp. 757-764.
Schalk, Isabelle J., et al., "Iron-Free Pyoverdin Binds to Its Outer Membrane Receptor FpvA in Pseudomonas Aeruginosa: A New Mechanism for Membrane Iron Transport", 2001, Molecular Microbiology, vol. 39, No. 2, pp. 351-360.
Albrecht-Gary et al., "Bacterial Iron Transport: Coordination Properties of Pyoverdin PaA, a Peptidic Siderophore of Pseudomonas aeruginosa", 1994. Inorg. Chem., 33 (26), pp. 6391-6402.
Henne, Walter A., et al., "Synthesis and Activity of a Folate Peptide Camptothecin Prodrug", (Aug. 9, 2006), Bioorganic & Medicinal Chemistry Letters, vol. 16, pp: 5350-5355.
Tang, Hailun, et al., "Prostate Targeting Ligands Based on N-Acetylated α-Linked Acidic Dipeptidase", (2003), Biochemical and Biophysical Research Communications, vol. 307, pp: 8-14.
Wosikowski, Katja, et al., "In Vitro and in Vivo Antitumor Activity of Methotrexate Conjugated to Human Serum Albumin in Human Cancer Cells", (May 2003), Clinical Cancer Research, vol. 9, pp: 1917-1926.
International Search Report and Written Opinion for PCT/US2007/023176 completed Aug. 4, 2008.
Wiener et al., "Targeting Dendrimer-Chelates to Tumors and Tumor Cells Expressing the High-Affinity Folate Receptor," Investigative Radiology, 1997; 32(12):748-754.

(56) References Cited

OTHER PUBLICATIONS

Paulos et al., "Ligand Binding and Kinetics of Folate Receptor Recycling in Vivo: Impact on Receptor-Mediated Drug Delivery," Molecular Pharmacology, 2004; 66:1406-1414.
He et al., "In vivo quantitation of rare circulating tumor cells by multiphoton intravital flow cytometry," Proc Nat Acad Sci USA, 2007; 104: 11760-11765.
Chen et al., "In vivo imaging of proteolytic activity in atherosclerosis," Circulation, 2002, 105: 2766-2771.
Mathias et al., "Synthesis of [99mTc]DTPA-Folate and Its Evaluation as a Folate-Receptor-Targeted Radiopharmaceutical", Bioconj. Chem., 2000; 11:253-257.
Linder et al., "In Virto & in Vivo Studies with α-and γ-Isomers of 99mTc-OXA-Folate Show Uptake of Both Isomers in Folate-Receptor (+) KB Cell Lines", Soc. Nucl. Med. Proc., May 2000; 41:5:119.
Ilgan et al., "99mTc-Ethylenedicysteine-Folate: A New Tumor Imaging Agent. Synthesis, labeling and Evaluation in Animals", Can. Biother. & Radiophar., 1998; 13:6:427-435.
Massoud et al., "Molecular imaging in living subjects: seeing fundamental biological processes in a new light", 2003, Genes Dev. 17: 545-580.
Caliceti et al., "Pharmacokinetic and biodistribution properties of poly9ethylene glycol)—protein conjugates", 2003, Adv. Drug Del. Rev. 55: 1261-1277.
Tamaki, et al., "PET in Oncology" Jpn J Cancer Clin, 2003, 49(6): 531-535.
Remington: The Science & Practice of Pharmacy, 21th Edition (Lippincott Williams & Wilkins, 2005).
Bendele et al., "Animal Models of Arthritis: Relevance to Human Disease", Toxicology Pathology, vol. 27, No. 1, pp. 134-142, 1999.
Tanaka, et al., "Digestive tract lesions and immunity," The Japanese Journal of Gastroenterology, 1994, vol. 91(2): 131-135.
Folate-FITC (http://www.medkoo.com/Anticancer-trials/EC-17.htm (downloaded on Aug. 8, 2013)).
Atherosclerosis (http://web.archive.org/web/20081207060136/http://en.wikipedia.oro/wiki/Atherosclerosis (archived on Dec. 7, 2008)).
Yang et al, Imaging Tumor Folate Receptors using radiolabeled folate and methotrexate, Jour Labelled Compounds and Radiopharmaceuticals, 1999, Sussex, GB, vol. Suppl 1, 42: S696-S697.
Ilgan et al., "Imaging tumor folate receptors using 111 IN-DTPA-methotrexate." Cancer Biother. Radiopharm., 1998, 13(3) pp. 177-184.
Akihiro H. et al., "Affinity for a-tocopherol transfer protein as a determinant of the biological activities of vitamin E analogs." Federation of European Biochemical Societies, 1997, vol. 409, pp. 105-108.
Kazuki S. et al., "Novel vitamin D3 antipsoriatic antedrugs: 16-En-22-oxa-1a,25-(OH)2D3 analogs," Bioorganic & Medicinal Chemistry, 2006, vol. 14, pp. 1838-1850.
Hisashi T. et al., "c-Fos protein as a target of anti-osteoclastogenic action of vitamin D, and synthesis of new analogs," journal article, The Journal of Clinical Investigation, 2006, vol. 116, No. 2, February, pp. 528-535.
Masato S. et al., "Synthesis and biological activities of new 1a,25-dihydroxy-19-norvitamin D3 analogs with modifications in both the A-ring and the side chain," journal article, Bioorganic & Medicinal Chemistry, 2006, 14(12) pp. 4277-4294.
Agoston E.S. et al., "Vitamin D Analogs as Anti-Carcinogenic Agents" Anti-Cancer Agents in Medicinal Chemistry 2006, 6(1), pp. 53-71.
Lonsdale, D., "A Review of the Biochemistry, Metabolism and Clinical Benefits of Thiamin(e) and Its Derivatives." Evidence-Based Complementary & Alternative Medicine: eCAM. Advance Access Publication, vol. 3, Feb. 2006, pp. 49-59.
Nosaka, K. et al., "Separate Determination of Anticoccidial Thiamine Analogs by High-Performance Liquid Chromatography." ActaA Vitaminol. Et Enzymol., 1984, vol. 6 92), pp. 137-142.
Kandiko, C.T. et al., "Inhibition of Rat Brain Pyruvate Dehydrogenase by Thiamine Analogs." Biochem. Pharmacology, vol. 37, No. 22, (1988) pp. 4375-4380.
Spry, C. et al., "A Class of Pantothenic Acid Analogs Inhibits Plasmodium Falciparum Pantothenate Kinase and Represses the Proliferation of Malaria Parasites." Antimicrobial Agents and Chemotherapy, Nov. 2005, pp. 4649-4657.
Sargent, D.R. et al., "Antimetabolites of Pantothenic Acid, Ureido- and Carbamoyl-Derivatives." Texas Reports on Biology and Medicine, 1975, vol. 33, No. 3, pp. 433-443.
Hanck, A.B. et al., "Dexpanthenol (Ro 01-4709) in the treatment of constipation." Abstract, Acta Vitaminol Enzymol, 1982, vol. 4 (1-2), pp. 87-97.
Kagechika, H. et al., "Synthetic Retinoids: Recent Developments Concerning Structure and Clinical Utility." J. Med. Chem., Sep. 22, 2005, vol. 48, No. 19, pp. 5875-5883.
Shealy, Y.F. "Synthesis and Evaluation of Some New Retinoids for Cancer Chemoprevention." Preventive Medicine, 1989, vol. 18, pp. 624-645.
Landuer, W. et al., "The Interaction in Teratogenic Activity of the Two Niacin Analogs 3-acetylpyridine and 6-aminonicotinamide," J Experimental Zoology, 1962, vol. 151, pp. 253-258.
Renz, P. et al., "Synthesis of 4-Aza-5, 6-diethylbenzimidazole and Biosynthetic Preparation of 4- and 7-Aza-5, 6-dimethylbenzimidazolylcobamide," Z. Naturforsch, 1997, vol. 52C, pp. 5287-5291.
Ayers, W.A., "Effect of Vitamin B12 and Analogs on the Respiration of a Marine Bacterium." Archives of Biochemistry and Biophysics, 1962, vol. 96, pp. 210-215.
Toraya, T. et al., "Immobilized Derivatives of Vitamin B12 Coenzyme and Its Analogs." Methods in Enzymology, 1980, vol. 67, pp. 57-66.
Ueda, M. et al., "Effect of Vitamin B12 Derivatives on Urinary Excretion of Methylmalonic Acid in Liver Diseases." Acta Med. Okayama, 1970, vol. 24, pp. 365-372.
Toraya, T. et al., "The Synthesis of Several Immobilized Derivatives of Vitamin B12 Coenzyme and Their Use as Affinity Adsorbents for a Study of Interactions of Diol Dehydrase with the Coenzyme." Journal of Biological Chemistry, 1980, vol. 255, No. 8, Apr. 25, pp. 3520-3525.
Takahata, Y. et al., "Synthesis, Properties and Microbiological Activity of Hydrophobic Derivatives of Vitamin B12." J. Nutr. Sci. Vitaminol., 1995, vol. 14, pp. 515-526.
Kamao, M. et al., "Determination of Plasma Vitamin K by High Performance Liquid Chromatography with Fluorescence Detection Using Vitamin K Analogs as Internal Standards." J. of Chromatography B., 2005, vol. 816, pp. 41-48.
Nishikawa, Y. et al., "Growth Inhibition of Hepatoma Cells Induced by Vitamin K and Its Analogs." Journal of Biological Chemistry, 1995, vol. 270, No. 47, Nov. 24, pp. 28304-28310.
Mack, D.O. et al., "The Carboxylation Activity of Vitamin K Analogs with Substitutions at Position 2, 3, or 5." Journal of Biological Chemistry, 1979, vol. 254, Apr. 25, pp. 2656-2664.
Mock, D.M. et al., "Urinary Biotin Analogs Increase in Humans During Chronic Supplementation: the Analogs are Biotin Metabolites." The American Physiological Society, 1997, pp. 83-85.
International Search Report for PCT/US2002/13890 completed Oct. 28, 2002 (Oct. 28, 2002).
Vesely, D.L. et al., "Biotin Analogs Activate Guanylate Cyclase." Molecular and Cellular Biochemistry, 1984, vol. 60, pp. 109-114.
Lambooy, J.P., "Riboflavin Analogs Utilized for Metabolism by a Lactobacillus Casei Mutant." Int. J. Biochem., 1984, vol. 16, No. 2, pp. 231-234.
Nielsen, P. et al., "Phosphates of Riboflavin and Riboflavin Analogs: A Reinvestigation by High-Performance Liquid Chromatography." Analytical Biochemistry, 1983, vol. 130, pp. 359-368.
Arya, P. et al., "Design and Synthesis of Analogs of Vitamin E: Antiproliferative Activity Against Human Breast Adenocarcinoma Cells." Bioorganic & Medicinal Chemistry Letters, 1998, vol. 8, No. 18, pp. 2433-2438.
Trachewsky, D. "Antihypertensive Effect of Riboflavin Analogs in Rats with Mineralocorticoid-Induced Hypertension." Hypertension, 1981, vol. 3, No. 1, Jan-Feb., pp. 75-80.

(56) References Cited

OTHER PUBLICATIONS

Skinner, W.A. et al., "Structure-Activity Relations in the Vitamin E Series. II. Derivatives of alpha-Tocopherol Substituted at the 5-Methyl Group." *J Med. Chem.*, 1962, vol. 12, pp. 64-66.
Neuzil, J. et al., "Vitamin E. Analogs: A New Class of Multiple Action Agents with Anti-Neoplastic and Anti-Atherogenic Activity." *Apoptosis*, 2002, vol. 7, pp. 179-187.
Politis, I. et al., " The Effect of Various Vitamin E Derivatives on the Urokinase-Plasmogen Activator System of Ovine Macrophages and Neutrophils." *British Journal of Nutrition*, 2003, vol. 89, pp. 259-265.
Wang, X. et al., "Vitamin E Analogs Trigger Apoptosis in HER2/erbB2-Overexpressing Breast Cancer Cells by Signaling Via the Mitochondrial Pathway." *Biochemical and Biophysical Research Communication*, 2005, vol. 326, pp. 282-289.
Kilbourn et al, Fluorine-18 labeling of proteins, 1987, J Nucl Med, 28: 462-470.
Coussens et al, Inflammation and cancer, 2002, Nature, 420: 860-867.
PCT International Search Report and Written Opinion for PCT Application No. PCT/US2010/026406, mailed Apr. 15, 2010.
Jallad et al, Dissertation Abstracts International, 2001, 65(5B), p2390.
Stummer et al, J Neurosurg, 2000, 93:1003-1013.
Kennedy et al, Dissertation Abstracts International, 2001, 65(5B), p2354.
Nisshoshi, 1994, The Japanese Journal of Gastoenterology, 91(2): 131-135.
Extended European Search Report for EP 02734139, completed Jun. 11, 2004.
International PCT Search Report and Written Opinion for PCT Application No. PCT/US2008/053293, completed Mar. 10, 2009.
International PCT Search Report and Written Opinion for PCT Application No. PCT/US2005/046708, completed Sep. 20, 2006.
Extended European Search Report for EP 05855293, completed Jun. 12, 2009.
Extended European Search Report for EP 04753487, completed Jun. 16, 2006.
International PCT Search Report and Written Opinion for PCT Application No. PCT/US2004/016667, completed Sep. 22, 2004.
International PCT Search Report and Written Opinion for PCT Application No. PCT/US2008/064711, completed May 19, 2010.
International PCT Search Report and Written Opinion for PCT Application No. PCT/US2006/037112, completed Nov. 14, 2007.
Reddy J A et al: "Expression and functional characterization of the beta-isoform of the folate receptor on CD34(+) cells," Blood, vol. 93, No. 11, Jun. 1, 1999, pp. 3940-3948, XP002300805.
Japanese Translation of PCT International Application No. 2005-519078 , PCT pub date:2003.
Japanese Translation of PCT International Application No. 2004-530678 , PCT pub date:2002.
Extended European Search Report for EP 07867348, completed Jul. 29, 2010.

* cited by examiner

Fig. 5 A-1 Fig. 5 B-1 Fig. 5 C-1
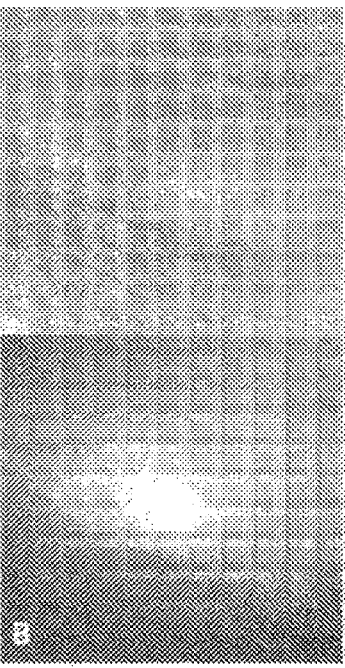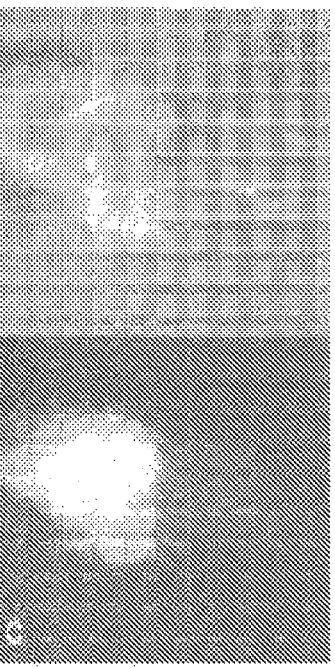
Fig. 5

Fig. 10 A-1  Fig. 10 B-1 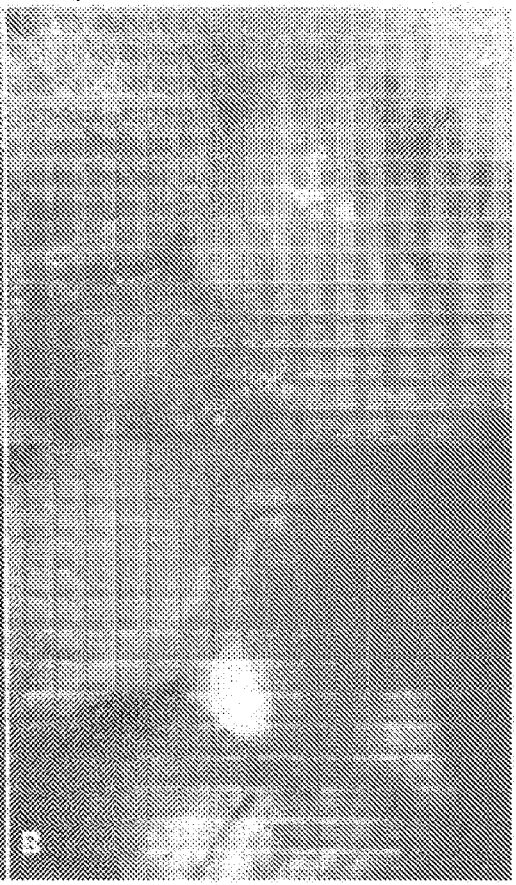
Fig. 10

FOLATE TARGETED ENHANCED TUMOR AND FOLATE RECEPTOR POSITIVE TISSUE OPTICAL IMAGING TECHNOLOGY

REFERENCE TO OTHER APPLICATIONS

This application is a continuation of U.S. application Ser. No. 13/468,010, filed May 9, 2012, now abandoned, which is a continuation of U.S. application Ser. No. 13/279,849, filed Oct. 24, 2011, now abandoned, which is a continuation application of U.S. application Ser. No. 10/360,001 filed Feb. 6, 2003, now U.S. Pat. No. 8,043,602, which claims the benefit of U.S. Provisional Application No. 60/355,417 filed Feb. 7, 2002, each of which is hereby incorporated by reference.

BACKGROUND AND SUMMARY

Cancer survival statistics establish the importance of early detection and thorough tumor resection for maximization of patient lifespan. Recent efforts to better achieve these objectives have focused on development of safer, more sensitive, and more discriminating imaging methodologies. MRI techniques rely on differences in water relaxivity between malignant lesions and healthy cells to achieve the desired contrast. PET imaging and methodologies generally exploit differences in metabolic fluxes between cancer and normal cells to allow tumor visualization. Some radiological imaging methods rely on the elevated passive vascular permeability of many neoplasms to achieve contrast with healthy tissues. Whereas radiological and magnetic resonance imaging modalities have clearly led the field in early detection, increased interest has arisen in developing optical imaging techniques for tumor diagnosis, largely because of safety concerns with the routine use of other methodologies.

Described herein is a method of use for a tumor targeting ligand, the vitamin folic acid, by which folic acid delivers optical probes to both primary and metastatic tumors overexpressing the folate receptor. Furthermore, an apparatus is disclosed to allow viewing of the tumor both excised and in-vivo. Upon laser excitation, derived images of normal tissues generally show little or no fluorescence, whereas images of folate receptor-expressing tumors display bright fluorescence that can be easily distinguished from adjacent normal tissue with the naked eye. Further, with the aid of appropriate optics, metastatic tumor loci of submillimeter size can also be visualized. The sharp distinction between tumor and normal tissues enabled by this technique finds application in the localization and resection of tumor tissue during surgery or in the enhanced endoscopic detection and staging of cancers.

According to a first embodiment of the present invention, a method of differentiating tumors from healthy cells in tissue is disclosed. The method includes the steps of providing a marker-folate conjugate, placing the marker-folate conjugate in contact with the tissue, and viewing the tissue.

According to another embodiment of the present invention, a method of resectioning tumor cells in tissue is provided. The method includes the steps of providing a marker-folate conjugate, exposing the tissue to the marker-folate conjugate, exposing the tissue to light, viewing the tissue, and resectioning the tissue based on the fluorescence of cells in the tissue.

According to still another embodiment of the present invention, a method of differentiating tumor cells from healthy cells in tissue is provided. The method includes the steps of providing a flourescein-ligand conjugate, enabling contact between the flourescein-ligand conjugate and the tissue, and viewing the tissue.

According to another embodiment of the present invention, an apparatus for differentiating tissue treated with a marker-ligand conjugate is provided. The apparatus comprises a light source configured to illuminate the tissue to cause tumor cells to appear different than healthy cells, a microscope including a lens, and a filter configured to reduce the amount of light from the light source that is transferred to the lens.

According to another embodiment of the present invention, an apparatus for differentiating in-vivo tissue treated with a marker-ligand conjugate is provided. The apparatus comprises a diffusing lens, a light source configured to emit light, the light configured to pass through the diffusing lens to illuminate the in-vivo tissue, a camera configured to receive images of the in-vivo tissue, and a filter configured to alter the amount of light that is received by the camera.

According to another embodiment of the present invention, an apparatus for differentiating in-vivo tissue treated with a marker-ligand conjugate is provided. The apparatus comprises an endoscope, a light source configured to emit light, the light configured to pass through the endoscope to illuminate the in-vivo tissue, a camera coupled to the endoscope and configured to receive images of the in-vivo tissue, and a filter configured to alter the amount of light that is received by the camera.

According to another embodiment of the present invention, a method of differentiating arthritic tissue from healthy tissue is provided. The method includes the steps of providing a marker-folate conjugate, placing the marker-folate conjugate in contact with the tissues, and viewing the tissues.

Additional features of the present invention will become apparent to those skilled in the art upon consideration of the following detailed description of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The detailed description particularly refers to the accompanying figures in which:

FIG. 5a includes pictures of M109 tumor tissue from a Balb/c mouse injected with folate-fluorescein (left) next to muscle tissue from the same mouse (right) under fluorescent illumination; FIG. 5a-1 includes pictures of M109 tumor tissue from a Balb/c mouse injected with folate-fluorescein (left) next to muscle tissue from the same mouse (right) under normal light;

FIG. 5b includes pictures of a subcutaneous L1210 tumor in a DBA mouse before dissection under fluorescent illumination; FIG. 5b-1 includes pictures of a subcutaneous L1210 tumor in a DBA mouse before dissection under normal light;

FIG. 5c includes pictures of an L1210 tumor (left) and muscle tissue (right) from a DBA mouse injected with folate-fluorescein under fluorescent illumination; FIG. 5c-1 includes pictures of an L1210 tumor (left) and muscle tissue (right) from a DBA mouse injected with folate-fluorescein under normal light;

Figure 1:
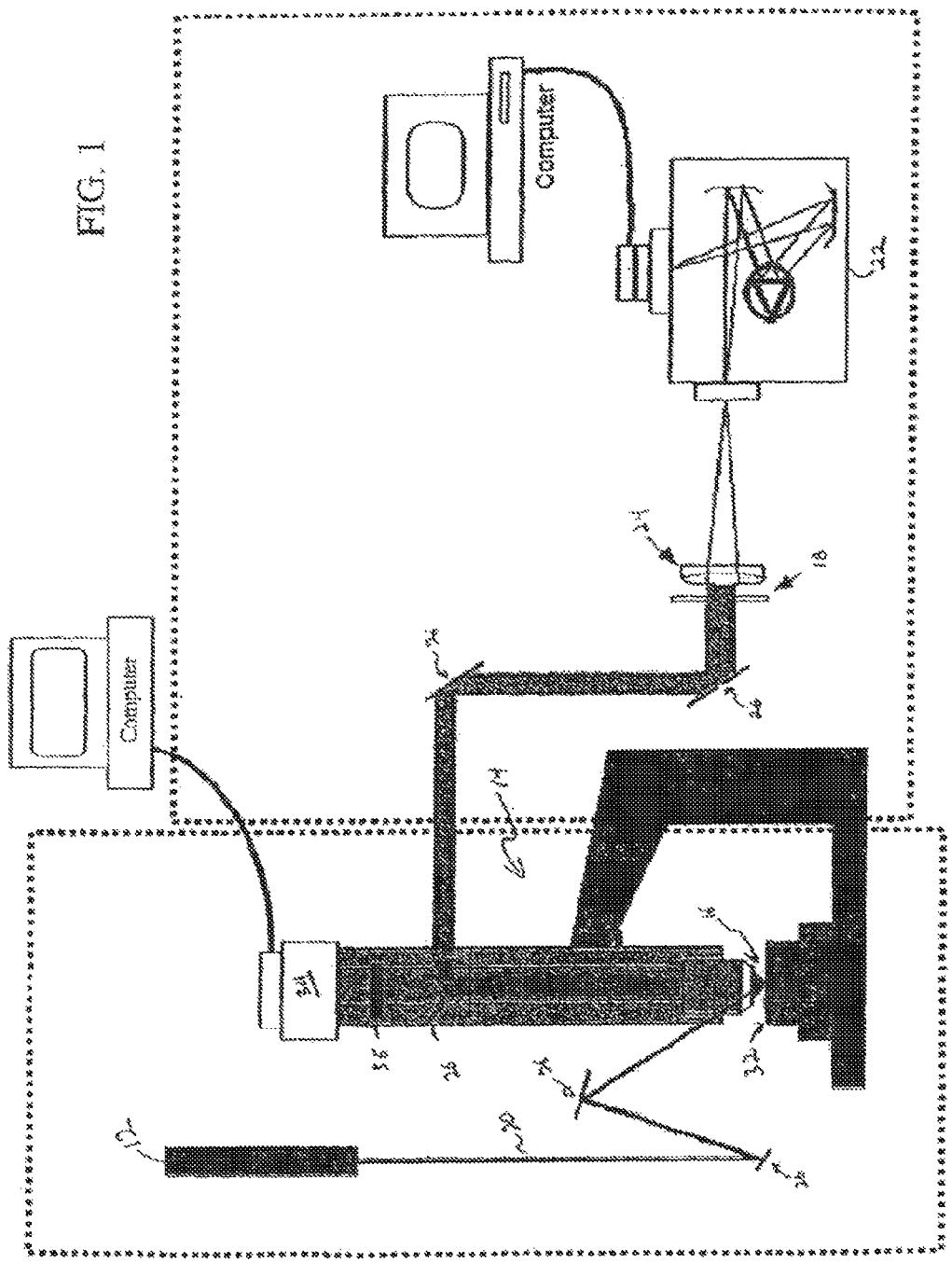
FIG. 1 is a schematic of the instrumentation used for obtaining images and spectra of excised and dissected tissues.
Figure 2:
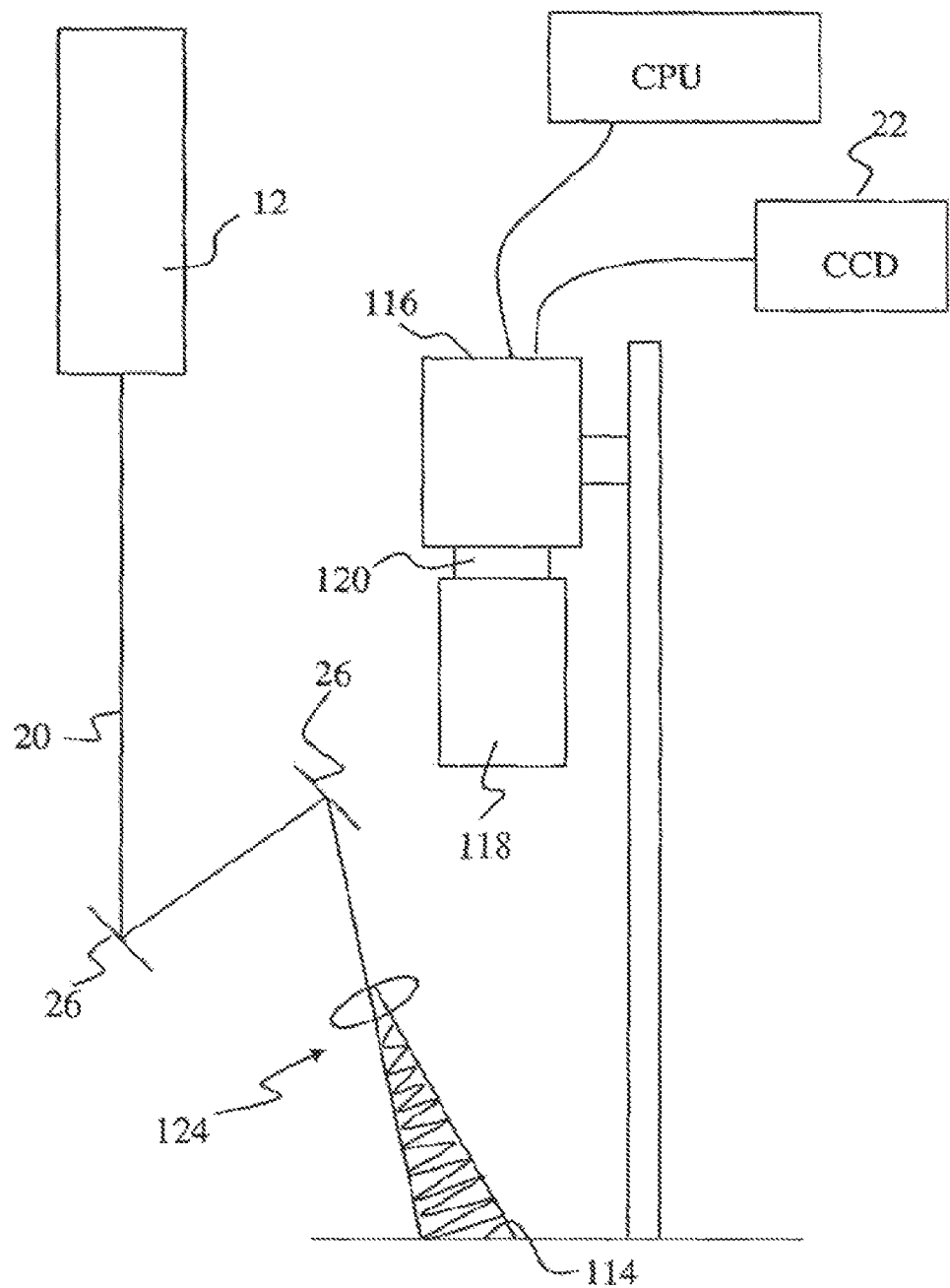
FIG. 2 is a schematic of instrumentation used for obtaining images and spectra of in-vivo tissues.
Figure 6:
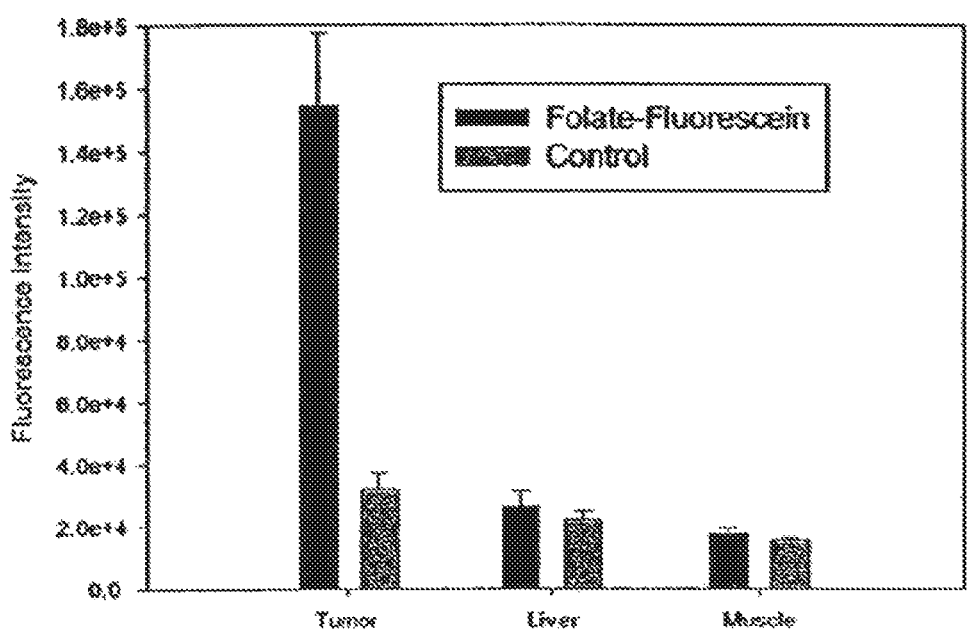
Figure 7:
Figure 8:
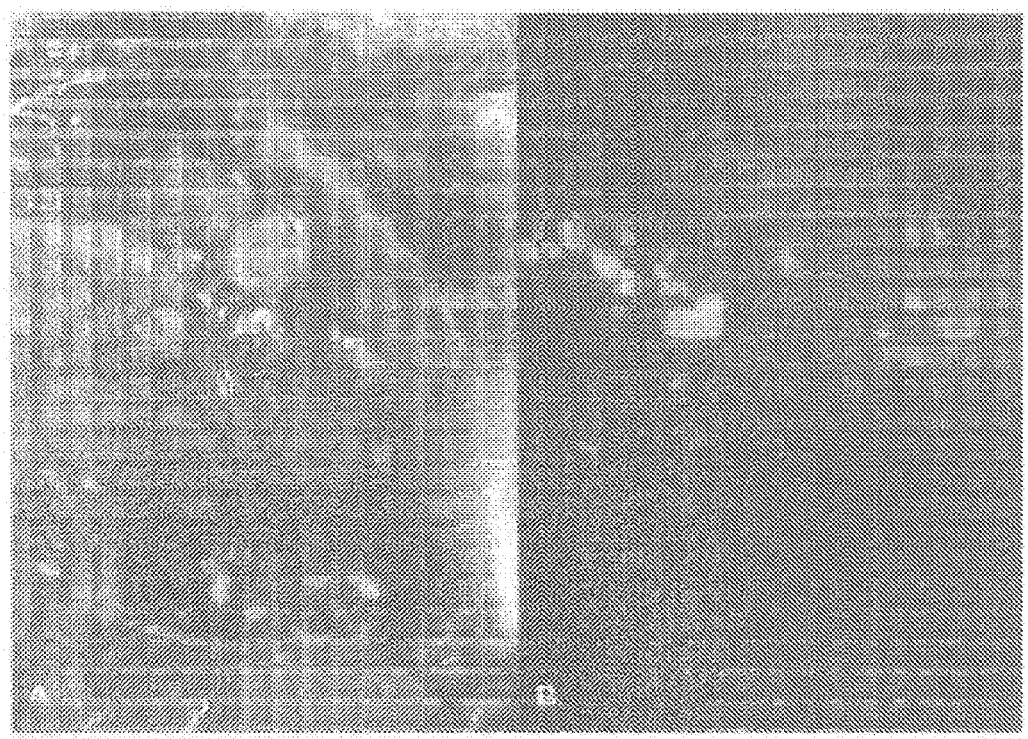
Figures 9A, 9B:
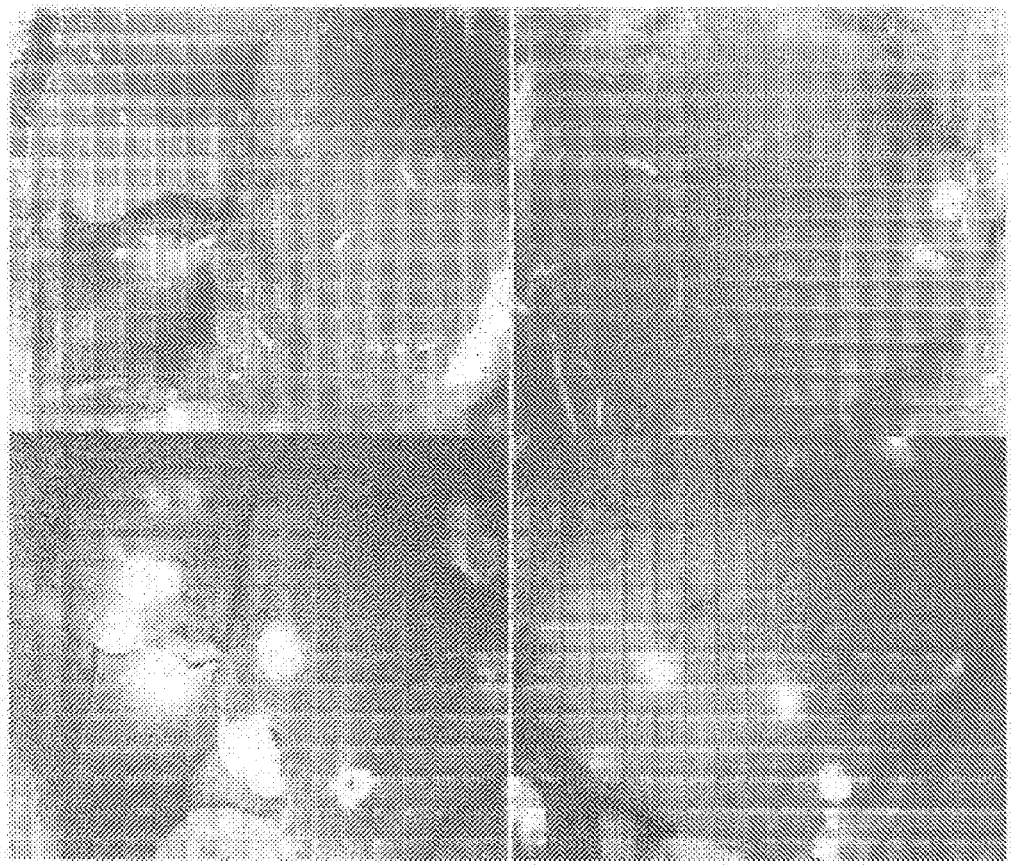
Figure 11:
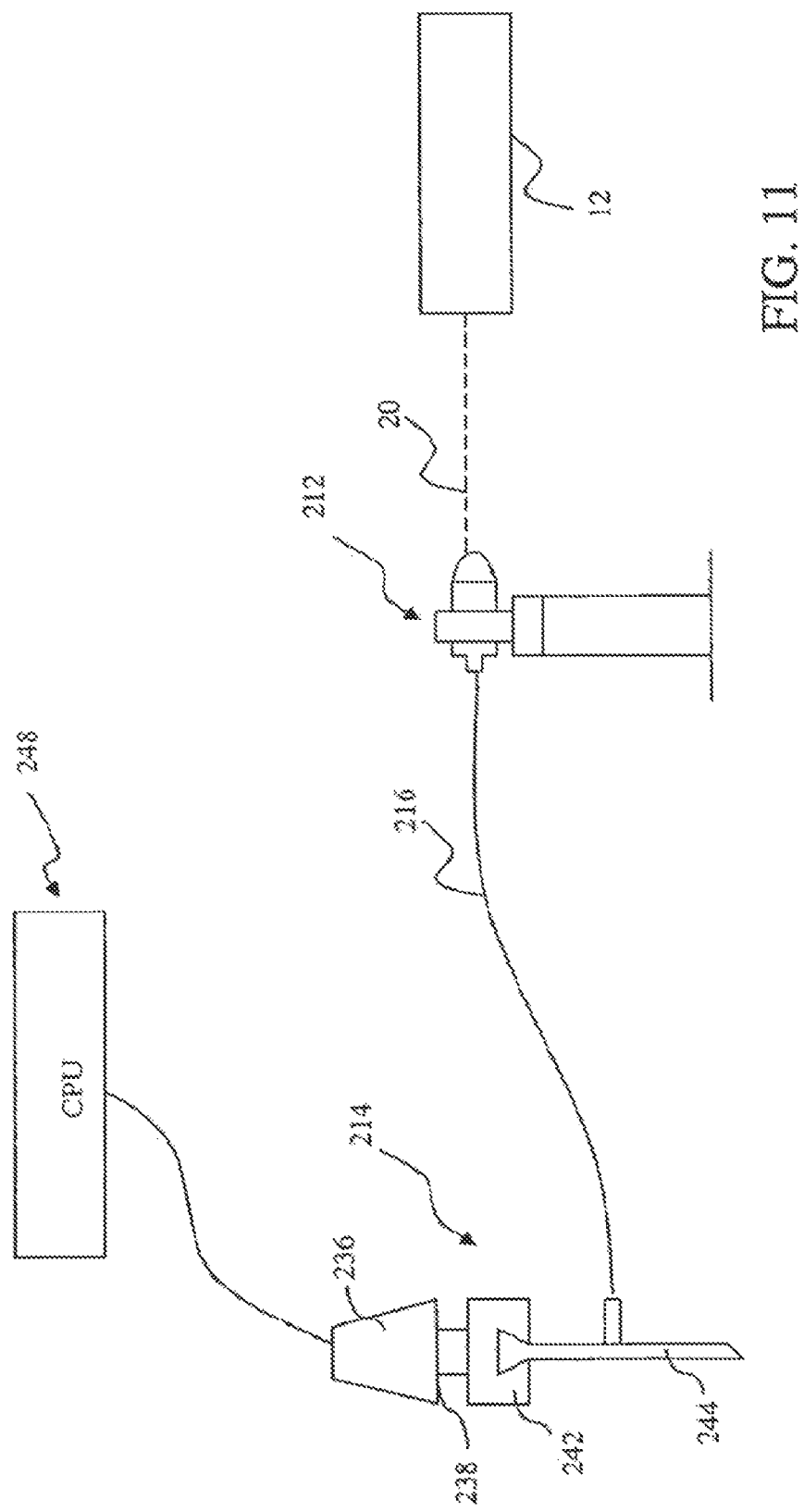
Figure 12:
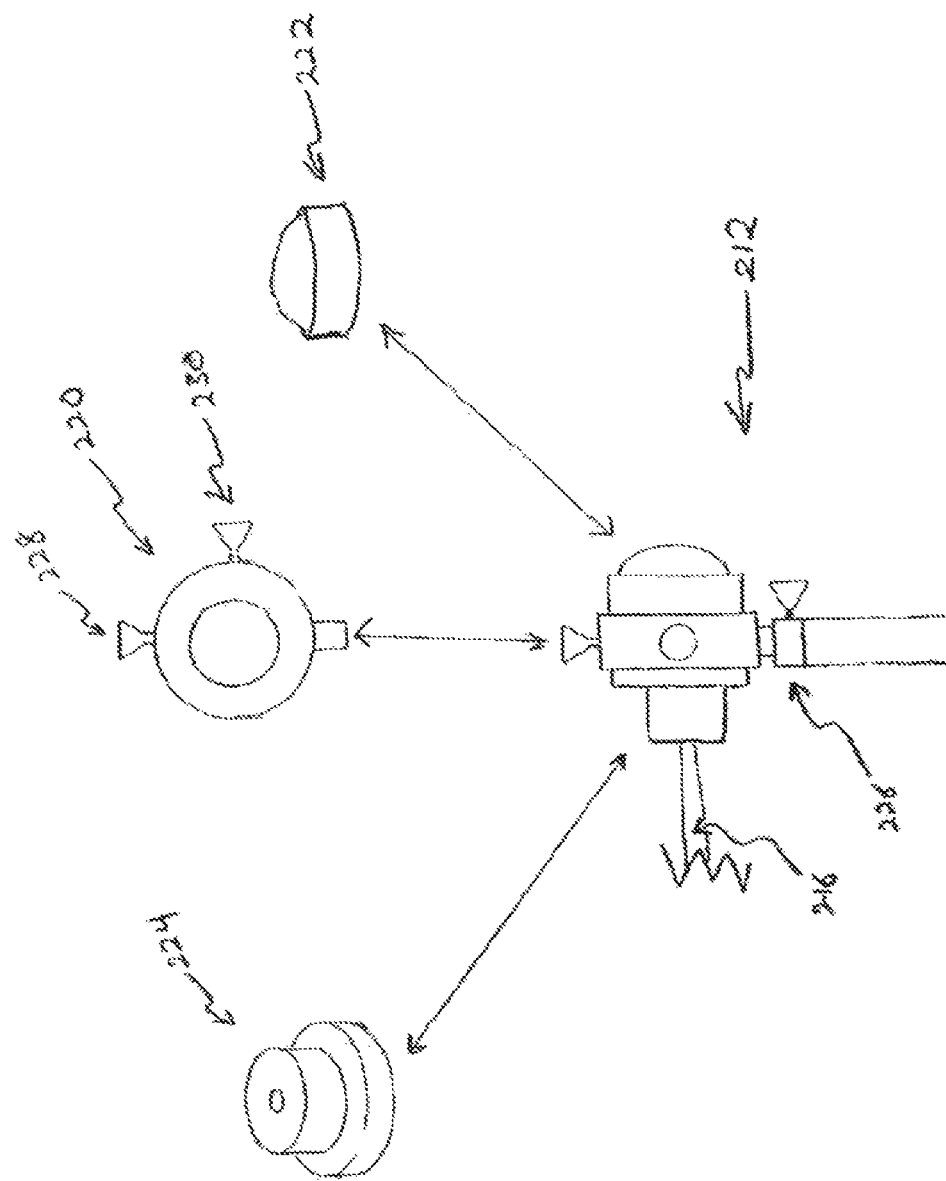
Figure 13:

FIG. 6 is a chart showing a fluorescence intensity comparison of tissues from mice injected with folate-fluorescein and from control mice with nothing injected;

FIG. 7 is a view of the peritoneal cavity of a Balb/c mouse with an M109 ip-induced tumor after injection of folate-fluorescein;

FIG. 8 includes views of M109 tumor nodules in a mouse lung after injection of folate-fluorescein under normal light and under fluorescent illumination;

FIG. 9a is a view of L1210 tumor nodules on the bottom of the liver of a DBA mouse under fluorescent illumination; FIG. 9a-1 is a view of L1210 tumor nodules on the bottom of the liver of a DBA mouse under normal light;

FIG. 9b is a view of L1210 tumor nodules on the top of the liver of a DBA mouse under fluorescent illumination; FIG. 9b-1 is a view of L1210 tumor nodules on the top of the liver of a DBA mouse under normal light;

FIG. 10a includes views of L1210 tumor nodules in the spleen of a DBA mouse after injection of folate-fluorescein under fluorescent illumination; FIG. 10a-1 includes views of L1210 tumor nodules in the spleen of a DBA mouse after injection of folate-fluorescein under normal light;

FIG. 10b includes views of L1210 tumor nodules in the muscle tissue on the neck of a DBA mouse after injection of folate-fluorescein under fluorescent illumination; FIG. 10b-1 includes views of L1210 tumor nodules in the muscle tissue on the neck of a DBA mouse after injection of folate-fluorescein under normal light;

FIG. 11 is a schematic of a system similar to the instrumentation of FIGS. 1-2 to allow imaging and spectra to be performed with an endoscope;

FIG. 12 is a schematic of an assembled and disassembled laser receiving apparatus which is part of the system of FIG. 11;

FIG. 13a is a view of rat paws without arthritis;
FIG. 13b is a view of rat paws with arthritis.

DETAILED DESCRIPTION OF THE EMBODIMENTS OF THE INVENTION

In-vivo tumor imaging requires the establishment of some type of measurable contrast between the tumor and surrounding normal tissues. The present imaging method exploits the overexpression of receptors for the vitamin folic acid on cancer cells to target attached imaging/contrast agents specifically to malignant cells.

The present folic acid-based targeting strategy utilizes i) the high affinity of folate for its cell surface receptor ($K_d \sim 10^{-10}$), ii) the inaccessibility of the receptor to circulating folates on those few normal cells that express it (the folate receptor on normal cells is primarily confined to the apical membranes of polarized epithelia where it is not easily accessed from the blood), and iii) the elevated expression of the folate receptor ("FR") on many tumor cells. Those tumors that commonly overexpress FR include cancers of the ovary, breast, kidney, lung, endometrium, myeloid cells, and brain.

During debulking surgery, where malignant loci can be difficult to identify, the presence of a fluorescent signal may assist with their localization. Further, when tumors are situated near the body surface and frequent analysis of tumor progression is required, the present optical imaging methodology can be repeatedly applied without danger of toxicity. Also, in the course of an endoscopic examination, fluorescence imaging can allow precise assessment of the location, size, and invasiveness of a tumor.

The present invention provides the ability to visualize folate receptor expressing cancer tissues in various peritoneal, subcutaneous, and metastatic murine tumor models following intravenous administration of a folate-fluorescein conjugate. Tumors as small as a few millimeters can be easily detected with the unaided eye. The present invention provides instrumentation to detect malignant lesions larger and smaller than 1 mm using folate-targeted fluorophores as aids in the localization and characterization of tumors during surgery and endoscopic examination as well as in excised tissue.

To obtain tumors for examination, M109 cells, a murine lung carcinoma cell line of Balb/c mouse origin, were grown subcutaneously in Balb/c mice. The tumors were excised under sterile conditions, minced into small pieces, and incubated for 4 hours in RPMI media (GIBCO, Grand Island, N.Y.) containing 200 U/ml of collagenase type 1A (Sigma, St. Louis, Mo.). M109 tumor cells were removed from the tumor pieces and washed twice with phosphate buffered saline (PBS) by centrifugation. The cells were then cultured overnight in folate-free RPMI (GIBCO, Grand Island, N.Y.), supplemented with 10% fetal calf serum (GIBCO, Grand Island, N.Y.), penicillin (100 IU), and streptomycin (100 µg/mL) (Sigma, St. Louis, Mo.). After removing remaining debris, the cells were passaged by treatment with trypsin (0.05%) (Sigma, St. Louis, Mo.) in $Ca^{+2}$ and $Mg^+$-free PBS. In order to retain high viability in Balb/c mice, M109 cells were discarded after the fourth passage in culture. L1210 cells, a lymphocyte-derived cell line of DBA mouse origin, were cultured in folate-free RPMI with a change of medium every 3-4 days.

To prepare the animals for in-vivo tumor imaging, Balb/c or DBA mice are placed on a folate-deficient diet (Dyets, Bethlehem, Pa.) three weeks prior to each experiment to lower the folate levels in the blood to the physiological range. Tumors are induced subcutaneously by injecting 100 µL of cell culture solution containing approximately 500,000 M109 or L1210 cells. Imaging of mice with subcutaneous tumors is performed when the tumors reach approximately 200 mm³ in size. For intraperitoneal (i.p.) tumors, approximately 500,000 M109 or L1210 cells are implanted in the peritoneal cavity and allowed to proliferate for approximately 2 weeks prior to analysis, which is sufficient time for tumor masses greater than 1 mm³ to appear. Metastatic tumors are initiated by injection of approximately 200,000 M109 or L1210 cells into the femoral vein, and the imaging is performed two weeks afterwards in a variety of tissues.

Figures 3A, 3B:
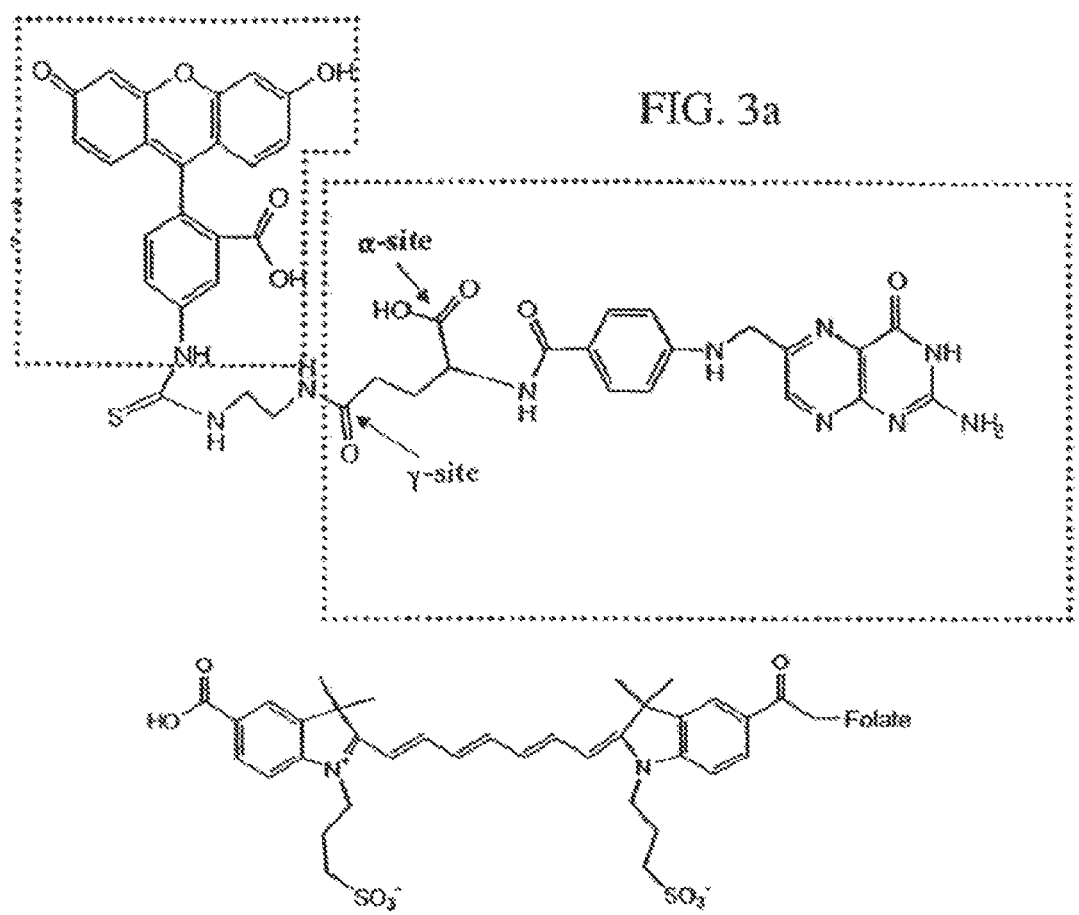
FIG. 3a shows the structure of folate-γ-fluorescein. MW 872. $C_{42}H_{36}N_{10}O_{10}S$.
FIG. 3b shows the structure of folate-indocyanine.

A folate-fluorescein conjugate, as shown in FIG. 3a and provided by Endocyte (West Lafayette, Ind.) (or the non-targeted control, fluorescein amine), is injected into the femoral vein by making an incision in the leg to expose the vein. FIG. 3a shows the conjugate provided by Endocyte having fluorescein amine bonded at the gamma carboxyl group of folic acid. A conjugate having fluorescein amine bonding at the alpha carboxyl group was also synthesized and provided similar results as the gamma bonded conjugate. 100 µL of a PBS solution containing 8.7 µL (10 nmol) of folate-fluorescein conjugate (or 3.3 µg (10 nmol) of fluorescein amine in the case of a control) is then injected. The wound is then closed using Vetbond (The Butler Co., Indianapolis, Ind.). Two hours following intravenous injection of folate-fluorescein, the tumor-bearing mice were euthanized and their tumors imaged using both tungsten lamp (direct view) and argon laser (fluorescence view) illumination. To allow the illumination of the tumors, three systems 10, 110, 210 have been created as shown in FIGS. 1, 2, and 11.

Laser Imaging and Spectral Analysis In-Vivo

Whole-tissue fluorescent imaging is performed using the imaging system 110 shown in FIG. 2 including an argon laser 12 (Spectra-Physics, Mountain View, Calif.) operating at 488 nm with a total laser power of 200 mW reaching the 2 cm sample field of view 114. Fluorescence is detected by a colored CCD camera 116 such as a JAI CV-53200N manufactured by Edmund Industrial Optics, Barrington, N.J. with a sensing area of 768×494 pixels and a pixel size of 8.4×98 $\mu m^2$. An f/5.6 152-457 mm 10×CCD zoom lens 118, also produced by Edmund Industrial Optics, Barrington, N.J., is used to collect fluorescence from the 2.0 cm×2.0 cm field of view 114. A band pass filter 120 with less than 80% T at 515-585 nm (Inter, Inc., Socorro, N. Mex.) is placed between the lens 118 and the CCD Camera 116 in order to reject laser light 20 and suppress tissue auto-fluorescence outside the fluorescein fluorescence band. The images are digitally acquired using SNAPPY software v. 4.0 manufactured by Play, Inc., Sacramento, Calif.

The light 20 of laser 12 is aimed via a plurality of mirrors 26 such that the light 20 passes through a diffusing lens 124 to illuminate the field of view 114 as shown in FIG. 2. The CCD camera 116 and SNAPPY software can then take a picture through the lens 118 and the filter 120. Likewise, the CCD camera 116 can register fluorescent spectra such as those shown in FIG. 5.

Laser Imaging and Spectral Analysis for Excised Tissue

Figure 4A:
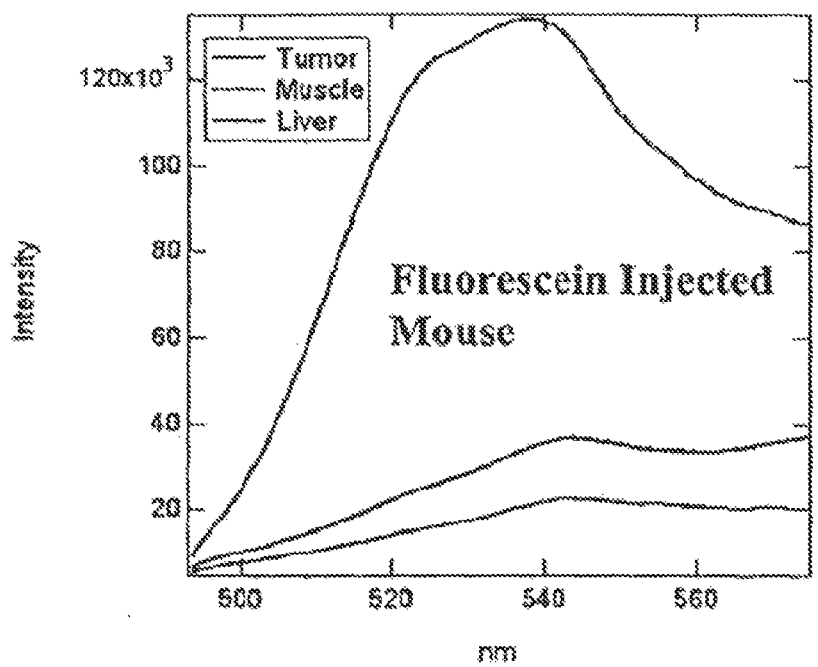
FIG. 4a is a chart showing emission spectra of tissues from a mouse injected with folate-fluorescein.
Figure 4B:
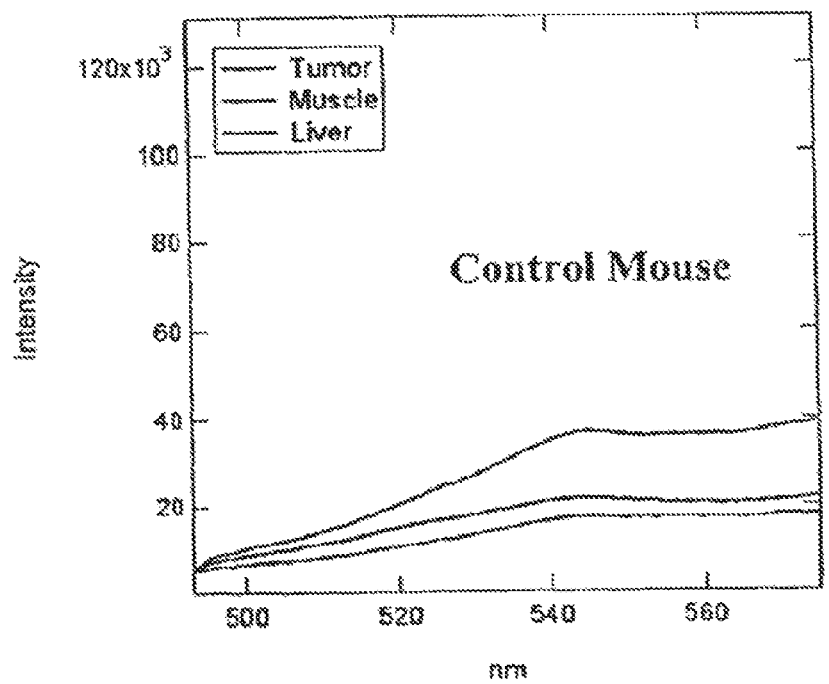
FIG. 4b is a chart showing emission spectra of tissues from a mouse with nothing injected.

FIG. 1 is a schematic of an apparatus used to acquire images and spectra of excised and dissected tissue. In this case, the laser 12 is used to illuminate a 5 mm diameter area of a sample placed on an OLYMPUS BH-2 microscope 14 stage (Olympus, Inc., Melville, N.Y.). The fluorescent light from the treated tissue is collected with a 4× objective 16 and directed from the sample toward a holographic Super-Notch filter 18 (HNF, Kaiser Optical, Ann Arbor, Mich.) using a 99% reflective mirror 26 placed above the microscope objective 16. The HNF 18 is used to reject the laser light 20 at 488 nm, and the fluorescent light transmitted through the HNF 18 is focused on the spectrograph 22 (Spectra Pro-150, Acton Research Corporation, Acton, Mass.) entrance (slit width=200 $\mu m$) using a lens 24 of 21 mm focal length. FIGS. 4a and b shows fluorescence spectra that are obtained with the thermoelectric cooled CCD 22 (ST6, SBIG Instruments, Santa Barbara, Calif.) with 375×242 pixels and a pixel size of 23×25 $\mu m^2$. The spectrograph 22 is equipped with a 600 g/mm grating tuned to a wavelength of 535 nm and spanning a 495 nm to 575 nm window on the CCD detector 22. The fluorescence spectra are acquired using KESTREL Spec software (Princeton Instruments, Trenton, N.J.) with an integration time of 5 s, and fluorescence wavelengths are calibrated against neon lamp calibration lines.

Once again, light 28 from an argon laser 12 is directed via mirrors 26 so as to illuminate tissue on a stage 32 of microscope 14. Any fluorescence is captured by camera 34 via filter 35, similar to filter 120, and by the spectrograph 22.

Spectra were taken of various tissues removed from mice two hours after an injection with 8.7 $\mu g$ of folate-linked fluorescein. Spectra were also taken of control samples taken from mice with nothing injected.

As seen in FIGS. 5a-c, tumors are significantly more fluorescent than adjacent normal tissues. In fact, the differences in fluorescence intensity were readily apparent to the naked eye without the assistance of optical equipment as shown in the upper pictures of FIGS. 5a-c. Therefore, folate-linked fluorophores are useful for optical imaging wherever tumor location allows access to incident and fluorescent light.

To more accurately quantify the difference in the targeted fluorescence between normal and malignant tissue, spectral properties of various tissues using more analytical spectrofluorimetric methods was examined. For this purpose, tissue samples from both folate-fluorescein injected and noninjected tumor-bearing mice were examined using a spectrograph equipped with laser 12 excitation. Although tumor tissue from injected mice consistently showed an approximately fivefold greater fluorescence than the autofluorescence of noninjected controls, liver and muscle tissues, which did not express the folate receptor, displayed no difference in fluorescence intensity, regardless of the presence or absence of folate-fluorescein pretreatment (FIG. 6). Therefore, these results strongly suggest that folate targeting is responsible for the enhanced fluorescence seen in the diseased tissue.

In order to test the ability of folate-fluorescein to facilitate detection of microscopic tumor nodules, metastatic tumors of M109 cell origin were induced by inoculation of cells either into the peritoneal cavity (ip) or femoral vein (iv) of the syngeneic mice. After allowing sufficient time for tumor growth, tumor loci were again imaged by intravenous administration of folate-fluorescein followed by laser excitation. As seen in FIG. 7, metastatic tumor nodules 50 smaller than 0.5 mm were readily observable in both lungs of the intravenously inoculated mice, and all tumor metastases fluoresced intensely compared to adjacent nonmalignant tissue. Similar results were also obtained in the intraperitoneal metastatic tumor model when the peritoneal cavity was opened and imaged as above.

To further explore the ability of folate-fluorescein to image small metastatic lesions, L1210 cells were also inoculated intravenously into syngeneic mice and the various anatomical regions were again imaged as above. Since L1210 cells are lymphocytic in origin and relatively small in size, they are capable of forming tumor nodules throughout the body after iv injection, rather than becoming entrapped primarily in the lung capillary network. As shown in FIG. 8, both the under surface (panel a) and the top surface (panel b) of the liver contained multiple microscopic nodules 50 that were clearly revealed under laser illumination. Further, the animal's spleen was almost entirely filled with minute tumor loci (FIG. 9a) and was consequently enlarged to roughly twice its normal size. Tumor nodules were also found in muscle tissue near the shoulder (FIG. 9b) and in the brain, spinal cord, and along the pleura. In fact, tumor nodules were seen in most tissues of the body and no nodules were identified that did not fluoresce under laser illumination.

Finally, a major limitation of this imaging methodology has been the requirement to expose the tumor before image collection. This requirement was mandated by the inability of visible light to penetrate most tissues more than a few mm deep. Therefore, to begin to examine whether the same technology might be adapted to noninvasive imaging of deeper tumor loci, a second folate conjugate linked to a longer wavelength fluorophore, namely indocyanine (lambda$_{ex}$=745 nm, lambda$_{em}$=785 nm) was constructed. The rationale for this construct derived from the fact that absorption of heme and related compounds reaches a minimum near 700 nm, allowing light of this wavelength to penetrate much farther into normal tissue (see structure in FIG. 3b). As seen in FIG. 10, folate-carbocyanine can image a subcutaneous M109 tumor in an intact animal, showing a significant fluorescent enhancement over adjacent normal tissue. Whereas the tumor-targeted fluorescein probe proved most effective in imaging malignant masses that could be directly excited with incident light, an indocyanine-based probe was preferred when the exciting light had to penetrate normal tissue in order to illuminate the transformed cells. Likewise, near infrared based probes are envisioned.

The efficacy of targeted imaging agents such as fluorescein, that reveal a malignancy when the tumor is easily exposed, is affected by the instrumentation 10, 110, 210 that can allow such illumination to occur. Therefore, two possible applications are specifically suggested herein for such fluorescent probes. First, the ability of highly fluorescent conjugates to reveal a tumor's location under direct illumination may be exploited to guide a surgeon's knife during tumor resection. For example, ovarian cancers, which are strongly folate receptor positive, are usually asymptomatic during early stages of the disease, resulting in initial diagnoses at stage III or IV in 70% of all patients. At these late stages, there is significant spread of the cancer throughout the peritoneal cavity, with lesions commonly attached to the omentum, intestines, and other internal organs. Current treatment for such advanced cancers involves debulking surgery followed by chemotherapy. Importantly, optimal tumor debulking has been shown to significantly increase the rate of patient survival, suggesting that if otherwise undetected malignant masses were to be removed, a further increase in survival might be realized. Use of folate-fluorescein or a related probe in conjunction with the appropriate intraoperative viewing lenses could conceivably enable this objective.

Second, in many cases, a patient must undergo a second-look surgery to determine whether relapse has occurred. In this situation, an optical method that could readily distinguish cancer from non-cancer tissue during an endoscopic exam could prove beneficial.

Such an endoscopic imaging system 210 is shown in FIGS. 11-12. The system 210 includes a laser 12, a laser receiving apparatus 212, an endoscopic device 214, and a fiber optic 216 physically and optically linking the laser receiving apparatus 212 to the endoscopic device 214. The laser receiving apparatus 212 includes a positioning post 218, a translating lens mount 220 coupled to the positioning post 218, a lens 222, and a fiber optic holder 224. The positioning post 218 has an attachment device 226 configured to couple to the lens mount 220. The positioning post 218 is also able to selectively couple to a surface to fix its position. Therefore, the lens mount 220 via the positioning post 218 is translatable along a Z-axis. The translating lens mount 220 includes X and Y translating knobs 228, 230 and a transmission void 232, and is coupled to the lens 222 and the fiber optic holder 224. The lens 222 is illustratively a Plano-Convex lens with a focal length of 25.4 mm, a diameter of 25.4 mm, and anti-reflection coated for 350-650 nm. The lens 222 is mounted to one side of the lens mount 220 and the fiber optic holder 224 is mounted to an other side of the lens mount 220 such that the lens 222 and a fiber optic 216 as held by the fiber optic holder 224 are aligned with the transmission void 232. The X and Y translating knobs allow the lens 222 to be moved up and down (Y-axis) and left and right (X-axis). Therefore, in combination with the positioning post 218, the lens mount 220 allows the lens 222 to be moved in three directions, X, Y, and Z. The fiber optic holder 224 includes a fiber holding void 234 and a surface 235 to mount to the lens mount 220. The fiber optic 216 is illustratively a Karl Storz fiber optic model no. 4965A having a first end received in the fiber holding void 234.

A second end of the fiber optic 216 is coupled to the endoscopic device 214 shown in FIG. 11. The endoscopic device 214 includes a camera 236, a filter holder 238, a filter (not pictured), an endoscope holder 242, and an endoscope 244. The camera 236 is illustratively a Karl Storz Vetcam XL that is coupled to a computer 248 for imaging purposes. The camera 236 is also coupled to the filter holder 238. Any light that enters a 237 lens of the camera 236 must pass through the filter holder 238 and the filter placed therein. The filter is similar to the band pass filter 120 and operates to reject laser light 20 and suppress tissue auto-fluorescence outside the fluorescein fluorescence band. However, it should be appreciated that the filter, and all other filters 18, 120, may be chosen to have different qualities if different lasers, different wavelength laser light, or different markers are used. The filter holder 238 is also coupled to the endoscope holder 242 which is in turn coupled to the endoscope 244. The endoscope 244 is illustratively a Karl Storz endoscope 3.5 mm×17 cm Model No. 64018US. The endoscope 244 is able to receive the second end of the fiber optic 216 therein and aim any light from the fiber optic 216 to the field of the endoscope 244.

Light is provided to the fiber optic 216 via the laser receiving apparatus 212 described above. The laser 12 is aimed at the lens 222 so that the laser light 20 can be guided and focused into the fiber optic 216. Rather than directly aiming the laser 12 at the lens 222, the laser 12 may also be directed to the lens 222 via mirrors 26. The laser receiving apparatus 212 may be adjusted along the X, Y, and Z axes via the knobs 228, 230 and positioning post 218 to achieve the optimal light 20 transmission to the field of the endoscope 244.

Folate-Fluorescein conjugates have also shown usefulness in detecting arthritis. Folate-targeted photosensitizers may be targeted to arthritic joints in that macrophages involved in rheumatoid arthritis have been found to express the folate receptor. Targeting a photosensitizer to arthritic joints allow phototherapy to be applied to the arthritic joint while preventing toxicity to other tissues. Imaging of joints, using apparatus such as those shown in FIGS. 1, 2, and 11, showed discernable contrast between arthritic, FIG. 13b, and non-arthritic tissues, FIG. 13a. One potential application of arthritis imaging is in the area of sport animal medicine. Race animals, such as dogs or horses, that have arthritis, could be diagnosed in an easy, inexpensive, and nonradioactive manner by using fluorescent imaging agents.

While the present invention has been disclosed as using folate based conjugates, it should be appreciated that it is also envisioned that folate receptor-binding analogs of folate and other folate receptor-binding ligands may also be used in place of folate. Furthermore, although the invention has been described in detail with reference to certain embodiments, variations and modifications exist within the spirit and scope of the invention as described and defined in the following claims.

What is claimed is:

1. A method of imaging a tumor during surgery, the method comprising the steps of:
   administering to a patient a folate conjugate comprising folate, or a folate receptor binding analog thereof, linked to a fluorescent agent; and
   imaging the patient during surgery to detect the tumor, wherein the tumor is smaller than 1 mm in size.

2. The method of claim 1 wherein the fluorescent agent is illuminated.

3. The method of claim 1 wherein the fluorescent agent is fluorescein.

4. The method of claim 1 wherein the fluorescent agent is a near infrared compound.

5. The method of claim 1 wherein the fluorescent agent is phycoerythrin.

6. The method of claim 1 wherein the fluorescent agent is indocyanine.

7. The method of claim 2 wherein the fluorescent agent is illuminated using a laser.

8. The method of claim 1 wherein the tumor is subcutaneous, wherein the folate conjugate causes a difference in fluorescence intensity between the tumor and normal tissue, and the difference is caused by a fluorescent emission capable of being transmitted through skin.

9. The method of claim 1 wherein the patient is an animal.

10. The method of claim 1 wherein the patient is a human patient.

11. The method of claim 1 wherein the tumor is imaged using an endoscopic device.

12. The method of claim 1 wherein the folate is an α-isomer of folate.

13. The method of claim 1 wherein the folate is a γ-isomer of folate.

14. The method of claim 1 wherein the imaging is optical imaging.

15. The method of claim 1 wherein the tumor is subcutaneous.

* * * * *